(12) United States Patent
Yoo

(10) Patent No.: US 10,265,696 B2
(45) Date of Patent: Apr. 23, 2019

(54) NUCLEIC ACID AMPLIFICATION DISK APPARATUS USING TEMPERATURE SENSITIVE POLYMER SYNTHESIS AND THE ANALYSIS METHOD USING THE SAME

(71) Applicants: RESEARCH BUSINESS FOUNDATION SUNGKYUNKWAN UNIVERSITY, Suwon-si (KR); CDgene Inc., Suwon-si (KR)

(72) Inventor: Jae Chern Yoo, Gwacheon-si (KR)

(73) Assignees: Research Business Foundation Sungkyunkwan University, Suwon-si (KR); CDgene Inc., Suwon-si (KR)

( * ) Notice: Subject to any disclaimer, the term of this patent is extended or adjusted under 35 U.S.C. 154(b) by 344 days.

(21) Appl. No.: 14/758,444

(22) PCT Filed: Dec. 27, 2013

(86) PCT No.: PCT/KR2013/012335
§ 371 (c)(1),
(2) Date: Jun. 29, 2015

(87) PCT Pub. No.: WO2014/104830
PCT Pub. Date: Jul. 3, 2014

(65) Prior Publication Data
US 2015/0328633 A1    Nov. 19, 2015

(30) Foreign Application Priority Data
Dec. 27, 2012  (KR) .................. 10-2012-0155242

(51) Int. Cl.
*B01L 3/00* (2006.01)
*G01N 21/64* (2006.01)
(Continued)

(52) U.S. Cl.
CPC ......... *B01L 3/502* (2013.01); *B01L 3/502715* (2013.01); *C12Q 1/6844* (2013.01);
(Continued)

(58) Field of Classification Search
CPC ....................................................... C12Q 1/68
See application file for complete search history.

(56) References Cited

U.S. PATENT DOCUMENTS 5,186,644 A    2/1993   Pawlicki et al.
5,186,844 A *  2/1993   Burd .................. G01N 21/07
                                             210/198.1
(Continued)

FOREIGN PATENT DOCUMENTS

CN     1771335 A      5/2006
CN   101166834 A      4/2008
(Continued)

OTHER PUBLICATIONS

Ross et al., Temperature measurement in microfluidic systems using a temperature-dependent fluorescent dye, Anal Chem. Sep. 1, 2001;73(17):4117-23.*

(Continued)

*Primary Examiner* — Aaron A Priest
(74) *Attorney, Agent, or Firm* — NSIP Law

(57) ABSTRACT

A nucleic acid amplification disk apparatus using a temperature sensitive polymer synthesis and the analysis method using the same, and more specifically, and the nucleic acid amplification device, and the analysis method using the nucleic acid amplification disk unit and the nucleic acid amplification disk for amplifying the Bacterial DNA or RNA, and the driving control section for controlling the nucleic acid amplification disk.

34 Claims, 11 Drawing Sheets

(51) Int. Cl.
| | |
|---|---|
| C12Q 1/6851 | (2018.01) |
| C12Q 1/6844 | (2018.01) |
| G01K 11/06 | (2006.01) |
| B01L 7/00 | (2006.01) |
| G01N 21/07 | (2006.01) |

(52) U.S. Cl.
CPC ............ *C12Q 1/6851* (2013.01); *G01K 11/06* (2013.01); *G01N 21/64* (2013.01); *B01L 7/52* (2013.01); *B01L 2200/10* (2013.01); *B01L 2200/147* (2013.01); *B01L 2300/023* (2013.01); *B01L 2300/0654* (2013.01); *B01L 2300/0803* (2013.01); *B01L 2300/0806* (2013.01); *B01L 2300/0861* (2013.01); *B01L 2300/0864* (2013.01); *B01L 2300/161* (2013.01); *B01L 2300/168* (2013.01); *B01L 2300/1822* (2013.01); *B01L 2300/1844* (2013.01); *B01L 2400/0409* (2013.01); *B01L 2400/0677* (2013.01); *B01L 2400/082* (2013.01); *C12Q 2565/625* (2013.01); *G01N 21/07* (2013.01); *G01N 2021/6439* (2013.01); *G01N 2021/6497* (2013.01)

(56) References Cited

U.S. PATENT DOCUMENTS

| | | | | |
|---|---|---|---|---|
| 6,063,589 | A * | 5/2000 | Kellogg | B01F 13/0059 366/DIG. 3 |
| 6,617,136 | B2 * | 9/2003 | Parthasarathy | C12Q 1/6844 435/6.11 |
| 6,734,401 | B2 * | 5/2004 | Bedingham | B01L 3/5025 219/388 |
| 6,752,961 | B2 * | 6/2004 | Kopf-Sill | B01L 3/502738 422/549 |
| 8,409,848 | B2 * | 4/2013 | Zeng | G06T 7/11 435/287.2 |
| 2004/0131345 | A1 * | 7/2004 | Kylberg | B01L 7/52 392/465 |
| 2004/0209258 | A1 * | 10/2004 | Parthasarathy | C12N 15/101 435/6.16 |
| 2008/0152546 | A1 * | 6/2008 | Bedingham | B01L 3/502738 422/400 |
| 2008/0277606 | A1 * | 11/2008 | Wang | B01L 3/5027 250/581 |
| 2009/0317896 | A1 | 12/2009 | Yoo et al. | |
| 2015/0027555 | A1 * | 1/2015 | Chen | B01L 3/502784 137/13 |

FOREIGN PATENT DOCUMENTS

| | | |
|---|---|---|
| CN | 101171346 A | 4/2008 |
| CN | 101522916 A | 9/2009 |
| JP | P2006-517801 A | 8/2006 |
| KR | 1020010015854 A | 2/2001 |
| KR | 1020040004014 A | 1/2004 |
| KR | 1020060091708 A | 8/2006 |
| KR | 1020070075742 A | 7/2007 |
| KR | 1020080005224 A | 10/2008 |
| KR | 1020090035465 A | 4/2009 |
| WO | 99/28500 A1 | 6/1999 |
| WO | WO 99/28500 A1 | 6/1999 |
| WO | 2004-077014 A2 | 9/2004 |
| WO | WO 2004/077014 A2 | 9/2004 |
| WO | 2006-088290 A1 | 8/2006 |
| WO | WO 2006/088290 A1 | 8/2006 |
| WO | 2006-118420 A1 | 11/2006 |
| WO | 2006-121266 A1 | 11/2006 |
| WO | WO 2006/118420 A1 | 11/2006 |
| WO | WO 2006/121266 A1 | 11/2006 |
| WO | 2008-016271 A1 | 2/2008 |
| WO | WO 2008/016271 A1 | 2/2008 |

OTHER PUBLICATIONS

Sanford et al, Fluorescence-based temperature control for polymerase chain reaction, Anal Biochem. Mar. 1, 2014;448:75-81. Epub Nov. 28, 2013.*
Samy et al., Method for microfluidic whole-chip temperature measurement using thin-film poly(dimethylsiloxane)/rhodamine B, Anal Chem. Jan. 15, 2008;80(2):369-75. Epub Dec. 15, 2007.*
Mohr et al., Numerical and experimental study of a droplet-based PCR chip, Microfluidics and Nanofluidics, Oct. 2007, 3:611.*
Jung et al., Microscale surface thermometry using SU8/Rhodamine-B thin layer, Sensors and Actuators A: Physical vol. 171, Issue 2, Nov. 2011, pp. 228-232.*
Gujit et al., Chemical and physical processes for integrated temperature control in microfluidic devices, Lab Chip, 2003,3, 1-4, Dec. 16, 2002.*
Bu et al., A temperature control method for shortening thermal cycling time to achieve rapid polymerase chain reaction (PCR) in a disposable polymer microfluidic device, Journal of Micromechanics and Microengineering, vol. 23, No. 7, Published Jun. 24, 2013.*
Avella-Oliver et al., Towards photochromic and thermochromic biosensing, TrAC Trends in Analytical Chemistry, vol. 79, May 2016, pp. 37-45.*
In Gi Baek, The Measurement of temperature field for nanoporous thin film using two-color laser-induced fluorescence method, Dept. of Mechanical Engineering Graduate School, Ajou University,12, 2007, pp. 1-58, Korea.
PCT international Search Report, dated Apr. 28, 2014.
David et al.Temperature Measurement in Microfluidic Systems Using a Temperature-Dependent Fluorescent Dye, Analytical. Chem. Sep. 1, 2001, pp. 4117-4123, vol. 73 No. 17.
Communications of Chinese Office Action dated Jan. 24, 2017 of Chinese Patent Application No. 201380068638.2, which corresponds to this application.
Office Action of co-pending U.S. Appl. No. 14/732,664 of present application.
Na, Won-hwi et al., "Non-contact temperature measuring method using the transparency change of the thermo-paint for high speed rotating disk", *CICS 2012 Thesis* 2012, 1 page in English and 2 pages in Korean).
Xiaoyu, Yu, "A Study on Phase Changing Valve on Microfluidic Chips", China Excellent Master's Thesis Full-Text Database Information Technology Series, Jul. 15, 2010 (6 pages in English and 7 pages in Chinese).
Ross, David et al., "Temperature Measurement in Microfluidic Systems Using a Temperature-Dependent Fluorescent Dye", *Analytical chemistry*, 73 (17), (pp. 4117-4123).

* cited by examiner

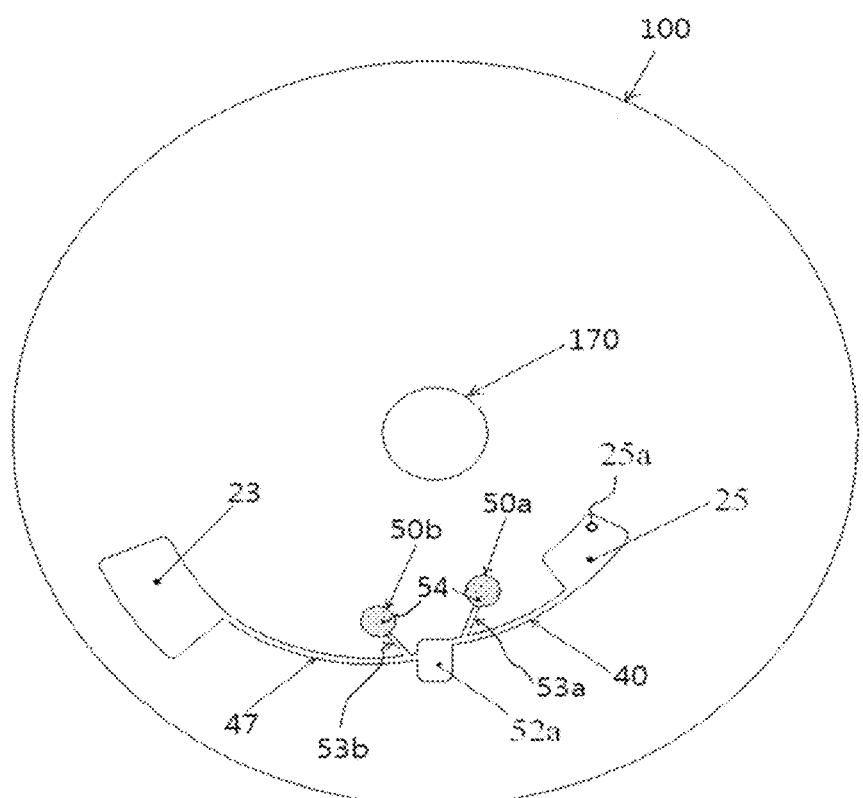
FIG.1B_A

FIG.1B_B
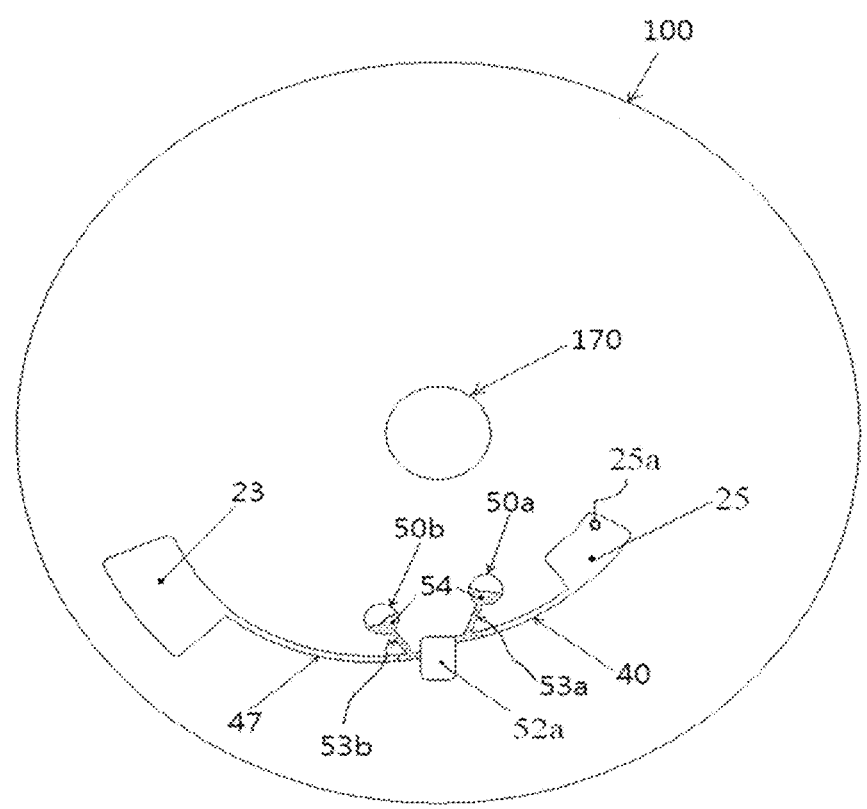

FIG.1C_A
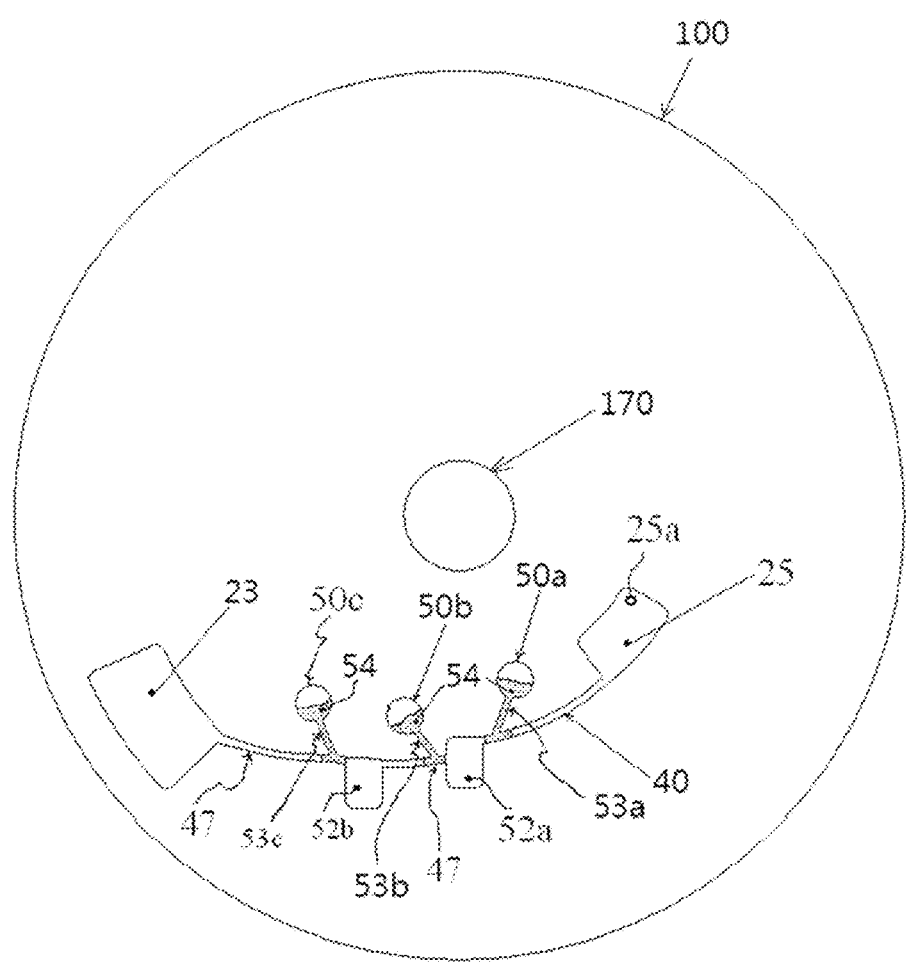

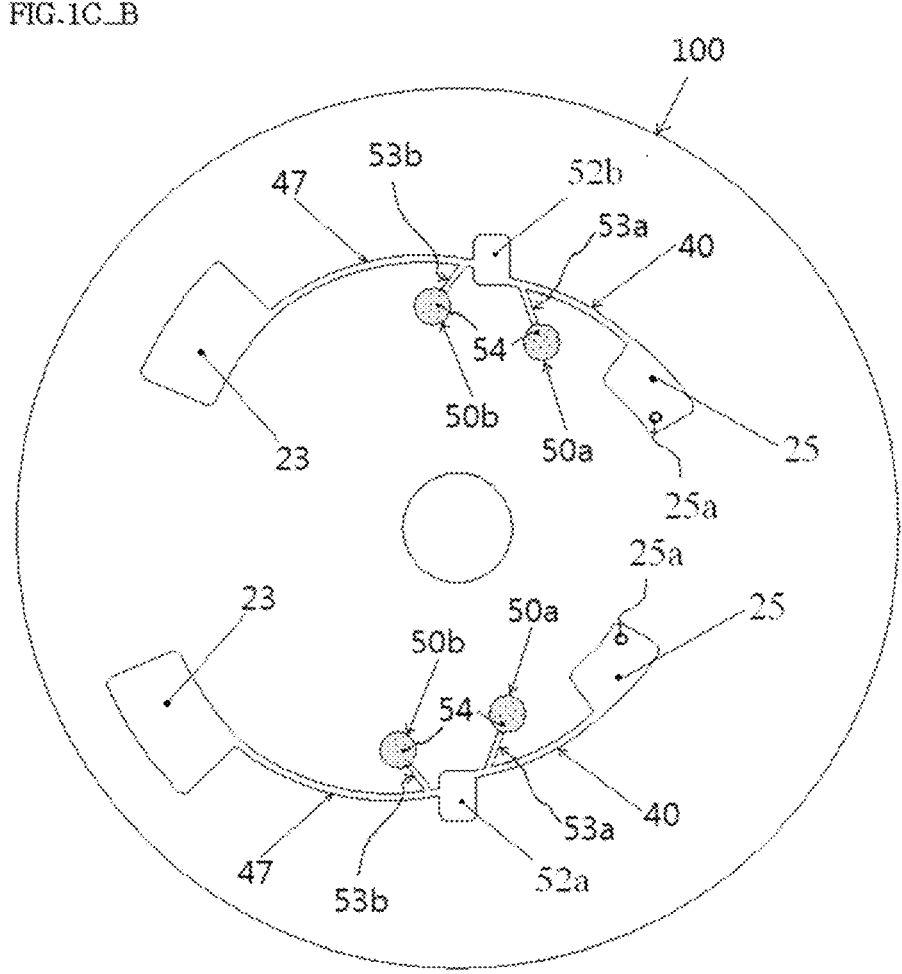
FIG.1C_B

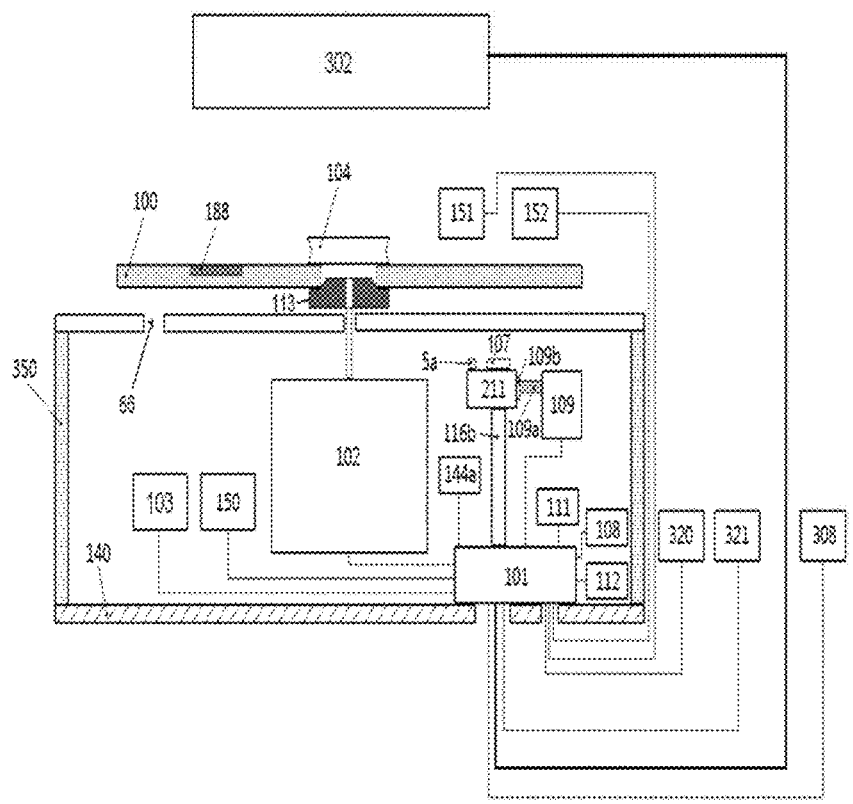

NUCLEIC ACID AMPLIFICATION DISK APPARATUS USING TEMPERATURE SENSITIVE POLYMER SYNTHESIS AND THE ANALYSIS METHOD USING THE SAME

CROSS-REFERENCE TO RELATED APPLICATIONS

This application claims the benefit under 35 U.S.C. Section 371, of PCT International Application No.: PCT/KR/2013/012335, filed on Dec. 27, 2013, which claims foreign priority to Korean Patent Application No.: 10-2012-0155242, filed on Dec. 27, 2012, in the Korean Intellectual Property Office, both of which are hereby incorporated by reference in their entireties.

TECHNICAL FIELD

Embodiments of the present invention, a nucleic acid amplification disk apparatus uses the temperature sensitive polymer synthesis to analyze, more specifically, embodies of the present invention relates to the nucleic acid amplification disk unit using the temperature sensitive polymer synthesis and the analysis method using the same, and more specifically, to the invention is the DNA necessary for the nucleic acid hybridization assay apparatus or the immunology verifying device or the nucleic acid amplification disk unit including the nucleic acid amplification disk in which the nucleic acid amplification process for amplifying RNA is arranged in aggregate and the driving control section for controlling the nucleic acid amplification disk and analysis method using these.

BACKGROUND ART

Until recently, clinical diagnostic analyzer for detecting a small amount of nucleic acid in the fluid was performed by the hand of the expert in series of processes, cell lysis process of pulverizing the cells of the sample, extracting process of DNA samples or RNA samples from the pulverized cell, process for preparing a DNA sample by the Reverse Transcription from RNA, process DNA template or target DNA nucleic acid amplification using the polymerase, dNTPm primer including various enzyme, and detection process of quantitatively measuring of polymer chain reaction of the product However, the nucleic acid amplification analyzer is expensive and can only be dealt by skilled experimenters and can only be purchased by centralized laboratory and hospitals for experiments.

Therefore, to overcome this problem, an affordable, easy to handle and automated nucleic acid amplification apparatus is desperately needed.

Recent design by integrating a number of bio and chemical processes in the form of a compact disk efficiency and cost-effectiveness has been improved and this compact disk analysis equipment is well exemplified in "Devices and methods for using centripetal acceleration to drive fluid movement on a microfluidics system" U.S. Pat. No. 6,063,589 "Methods and devices for removal of organic molecules from biological mixture using an anion exchange material that includes a polyoxyalkylene" US Patent Application Publication No.: 2004/0209258 A1: "Biological sample processing methods and compositions that include surfactants" U.S. Pat. No. 6,617,136 B2: "Enhanced sample processing devices, and systems and methods" U.S. Pat. No. 6,734,401 B2: "Apparatus and method for continuous centrifugal blood cell separation" U.S. Pat. No. 5,186,844 and "Modified siphons for improving metering precision" U.S. Pat. No. 6,752,961.

The experiment analysis apparatus of this form integrates multiple chambers performing biological or chemical process in the disk and has an advantage of accurately performing various analysis automatically at low cost using small quantity samples and reagent by centrifugal forces created by rotation of the disk.

But the heating DNA was essential for a nucleic acid amplification, it had been being regarded as the impossible technology to measure a temperature of the DNA sample in the disk chamber when disk is rotating.

Therefore, in the past analysis equipment, the temperature of the disk inside was indirectly measured utilizing the temperature of around the disk. Consequently it had the fatal problem that the accuracy about the temperature measurement in the disk inside was greatly reduced.

According to an embodiment of the present invention, by integrating every process and temperature sensitive polymer synthesis needed for the nucleic acid amplification on the compact disk shape board, the process of analyzing uses nucleic acid amplification apparatus using temperature sensitive polymer synthesis that directly measures the temperatures of DNA samples in the disk chamber.

SUMMARY OF THE INVENTION

Problem to Solve

Embodiments of the present invention are devised to solve the problems of the traditional techniques. One or more embodiment are to directly measure the temperatures of the DNA samples in the chamber by integrating the temperature sensitive polymer synthesis in the disk chamber and controlling the temperature in the chamber by feed backing the temperature into the temperature controller and to automatically perform the whole process of nucleic acid amplification.

Analysis method provides nucleic acid amplification disk apparatus using whole nucleic acid amplification integrated temperature sensitive polymer synthesis in a real time measurement of nucleic acid amplification product is achieved by preparation process to amplify DNA or RNA in the sample like blood, virus, bio material, or bacterial.

Specifically, the blood, the virus, in order to amplify the DNA or RNA contained in the sample, such as a biomaterial or a bacterial preparation from the nucleic acid amplification process output product the front-end of the nucleic acid amplified from the real-time measurement of the integrated is temperature sensitive to provide an analysis method using a nucleic acid amplification using the disk apparatus and polymer composites.

Means to Solve the Problem

An embodiment of the present invention, to control the DNA heating, and temperature of the DNA sample is measured with a temperature sensitive polymer synthesis.

Hereinafter, an embodiment of the present invention, samples is named the liquid removing the remnant from the blood serum obtained from sample such as sample is the whole blood, plasma, blood serum, feces, urine, food and bacteria, and plasma or these.

Hereinafter, an embodiment of the present invention, either the nucleic acid amplification disk or the "disk" can be used as the same meaning.

According to an embodiment of the present invention, the nucleic acid amplification disk apparatus using the temperature sensitive polymer synthesis includes a nucleic acid amplification disk, a motor for rotating the nucleic acid amplification disk, a driving controller including optical temperature sensor for measuring chamber temperature of the nucleic acid amplification disk and the temperature controller for controlling chamber temperature of the nucleic acid amplification disk, a sample inlet for inputting the sample, a centrifugal chamber for acquiring specimen from the sample by removing remnant or separating and storing the plasma or serum from the whole blood by centrifugal force; a remnant chamber for storing the remnant; a washing chamber storing washing buffer; a preparation chamber preparing DNA samples by separating refined DNA, RNA by removing impurity using the washing solution after cell lysis or by performing the reverse transcription for RNA; a nucleic acid amplification chamber stores enzymes necessary for nucleic acid amplification and buffer solution to perform DNA amplification, and fluid path by connecting the chambers for liquid flow.

An embodiment of the present invention, it is preferred that the centrifugation chamber is coated by the hydrophilicity paint, however, it is not limited thereto Hydrophilicity coating of the centrifugation chamber is help injecting smoothly for hydrophilicity sample through the sample inlet port. Generally, the sample has hydrophilic property.

The nucleic acid amplification disk may further include the metering chamber for supplying a predetermined quantity of sample to the preparation chamber.

The nucleic acid amplification disk may further include a sample movement channel in which sample moves with the hydrophilic fluid movement.

During centrifugal separation, the nucleic acid amplification disk includes, in the centrifugal 4 separation chamber, sample detainment channel between the centrifugal separation chamber and sample movement chamber to detain the sample as it is.

Because the surface of the sample movement channel is hydrophilic, sample in the sample chamber that was detained by the sample detainment channel during the rotation of the disk can be moved to sample movement channel by hydrophilic sample movement when the disk stops its rotation.

It is preferred that the nucleic acid amplification chamber stores buffer fluid including polymerase, dNTP, primer, and different kinds of enzyme.

The preparation chamber includes a lysis buffer for pulverization of the cell and a magnetic bead that combines with an exposed DNA from the pulverized cell by affinity. In this case, the nucleic acid amplification disk further includes the elution buffer chamber for storing a resuspension buffer or an elution buffer.

The magnetic bead is successively washed using the wash buffer and the impurity is removed from the preparation chamber. Finally the resuspension buffer or the elution buffer is inflowed into the preparation chamber and purely refined DNA is obtained if the elution process performs. The refined DNA is flowed into the nucleic acid amplification chamber and the nucleic acid amplification process is performed. The nucleic acid amplification disk may further include a DNA movement channel and a DNA movement control valve.

Instead of using a magnetic bead, the preparation chamber can be replaced by a silica bead which can combine with the DNA exposed from cell by affinity. At this time, the preparation chamber may further include the magnetic ball with the silica bead.

While the silica bead is washed using the wash buffer the magnetic ball is stirred with the magnetic force of an external permanent magnet from and the impurity is efficiently removed from the preparation chamber and an efficient DNA and silica bead bond is induced at the same time.

The magnetic bead is successively washed using the wash buffer and the impurity is removed from the preparation chamber. Finally the resuspension buffer or the elution buffer is inflowed into the preparation chamber and purely refined DNA is obtained if the elution process performs.

The refined DNA is flowed into the nucleic acid amplification chamber and performs the nucleic acid amplification process.

A diameter of the magnetic ball and silica bead are small enough not to pass through the DNA movement channel is preferred.

It is preferred that the nucleic acid amplification chamber is thin film coated with the temperature sensitive polymer synthesis.

An embodiment of the present invention, the nucleic acid amplification chamber stores the buffer solution including all kinds of the enzymes such as a dNTP, a primer, etc. and the nucleic acid amplification disk includes a separate polymerase chamber for storing the polymerase.

The driving controller includes a turn-table for mounting a nucleic acid amplification disk, a motor for rotating the nucleic acid amplification disk, a fluorescence sensor sense for analyzing a product of nucleic acid amplification quantitatively, the temperature controller for heating or cooling a nucleic acid amplification disk apparatus, a tray for allowing loading or un-loading of the nucleic acid amplification disk, optical temperature sensor for measuring the temperature of the inside of the nucleic acid amplification chamber, and a case for encapsulating the driving controller.

The disk is a circular disk having a diameter of any one of 120 mm, 80 mm, or 60 mm and a thickness in a range of 1.2 mm to 10 mm, however it is not limited thereto.

After excitation by the light source, the fluorescence sensor senses fluorescence radiated from the fluorescent material in the nucleic acid amplification chamber.

It is preferred that the temperature controller may include a heater and a cooler.

A fluid movement can be achieved by the centrifugal force generated by the fluid is the rotation of the disk, the hydrophilic fluid movement by a hydrophilic channel, or a fluid movement by a capillary phenomenon of fluid path.

The fluid path channel in which the fluid in the disk surface for the injection molding process flows and chamber which stores liquid are formed at the disk.

The case may further include, a display unit for displaying a status of a nucleic acid amplification progress, and a button input part for controlling operation on/off, or operation time and cycle number of the nucleic acid amplification.

The temperature measurement of the liquid stored in the nucleic acid amplification chamber by the optical temperature sensor is preferred.

An embodiment of the present invention, nucleic acid amplification apparatus may indirectly control a temperature of the nucleic acid amplification chamber by heating or cooling an atmosphere of case inside portion or which the amplifying apparatus cools.

An embodiment of the present invention, the temperature controller directly controls the nucleic acid amplification chamber.

The temperature controller directly or indirectly heats and/or cools the nucleic acid amplification chamber temperature by selecting one or more combinations of peltier device that can heat or cool, combination of a compressor and a radiator, a heating coil and a ventilation fan, an ultrasound heater, an illumination lamp or a laser implemented light illumination heater.

The nucleic acid amplification chamber, further includes a black film, to be heated by the lighting illumination heater. The black film absorbs heat heated with the light radiation heater and heat indirectly a liquid in the nucleic acid amplification chamber.

Preferably, the black film is any one of a heat-resistant film which does not melt with the light radiation heater or a metallic film which has a black coating layer The heat-resistant film is an aramid film, a Polyethylene Terephthalate PET film, and a polyimide film are preferred.

According to an embodiment of the present invention, preferably, the nucleic acid amplification chamber, further includes a black paint coated layer, is heated by the light radiation heating apparatus. The black paint absorbs heat and is heated with the light radiation heating apparatus and indirectly heat the liquid in the nucleic acid amplification chamber.

It is preferred that the black paint is heat resistant that does not melt by the light radiation heating apparatus.

It is preferred that the light radiation heating apparatus is a heater or laser beam generator including infrared lamp and high intensity LED.

The near infrared ray lamp with 20 Watt or 100 Watt is preferred.

The temperature controller further includes a circulating fan which can compulsory circulate air.

When using the heating coil and the ventilation fan, air inside the case is heated by the heating coil mounted on the ventilation fan and cooled by the ventilation fan to inlet outside cold air.

The heating coil heats the internal air of the case and the ventilation fan, mounted on the heating coil, cools the internal air by inflowing the external cold air.

The temperature controller may further include a fan shutter. The fan shutter is closed while heating the case inner portion and is opened while cooling the case inner portion. Thus, an insulation or a ventilation with the outside of the case can be converted each other.

It is preferred that the heating coil is arranged on the tray.

It is preferred that the cooling of the liquid material in the nucleic acid amplification chamber is controlled by the rotation of the disk. The heat release rate at the chamber surface increases and the cooling rapidly occurs while rotating the disk.

In another embodiment of the present invention, Phase change material (PCM) door is installed at the entrance and exit of the nucleic acid amplification chamber to prevent the liquid with active evaporation effect due to high temperature from moving to neighboring chamber when the liquid crystal fluid in the nucleic acid amplification chamber is heated.

The PCM door includes the capillary channel for PCM being fused in the PCM chamber which stores the phase change material PCM in which the look of the material is changed according to the temperature into solid or the liquid state and PCM chamber heating and draining from the PCM chamber and sealing hermetically in the entrance and exit of the nucleic acid amplification chamber.

Inside of PCM chamber, is coated with the black body or includes a micro heating particle which can absorb a light if light illuminates on the PCM, and generate a heat In this case, the heat of the external laser beam is absorbed and thus the PCM in the PCM chamber is easily fused. A black hot melt adhesive is preferred as the PCM.

Solid PCM in the PCM chamber is heated into liquid by the laser when the entrance and exit of the nucleic acid amplification chamber needs to be closed and the capillary channel connecting the PCM chamber and the nucleic acid amplification chamber is filled by the capillary effect.

Moreover, the laser heating is suspended if the liquid phase change material fills up the capillary channel and an entrance and an exit of the nucleic acid amplification chamber is closed from the neighbor chamber if the phase change material is the solid-state.

The optical temperature sensor may include a temperature sensitive fluorescence dye coated in the nucleic acid amplification chamber, and the laser beam generator and an optical sensor.

The temperature sensitive fluorescence dye changes an emission intensity of the fluorescence dye changes according to the liquid temperature in the nucleic acid amplification chamber.

Therefore, the temperature can be known by measuring the emissive intensity of the fluorescence by optical sensor according to the laser excitation.

According to an embodiment of the present invention, it is preferred to any one of dye is used such as a rhodamine B, a parylene, a fluorescein, a phosphor and the temperature sensitive fluorescence dye which an emissive power of the fluorescent light is changed according to temperature.

A rhodamine B is excited at about wavelength 553 nm when melting in the methanol and emits the fluorescent light of 627 nm wavelength emission is preferred.

A Parylene is excited at about wavelength 436 nm when melting in the tetrahydrofuran and emits a fluorescent light of 447 nm wavelength.

The rhodamine B and the parylene have characteristics of an increase in temperature according to decrease in amount of fluorescent light and can measure the temperature by measuring the amount of fluorescent light because it uses inverse proportionate.

According to an embodiment of the present inventions, to coat the temperature sensitive fluorescent dyes in the nucleic acid amplification chamber, temperature sensitive fluorescent dyes melts in acetone and mixes with photo resist by forming temperature sensitive polymer synthesis.

A "SU-8" manufactured by MicroChem is a photoresist.

According to an embodiment of the present inventions, to coat the temperature sensitive fluorescent dyes in the nucleic acid amplification chamber, melting a temperature sensitive fluorescent dyes in a volatile polar solvent, and mixing with a polymer for forming temperature sensitive polymer synthesis.

An acetone, a methanol or an ethanol are preferred as the volatile polar solvent.

The polymer is selected from any one of Polydimethylsiloxane PDMS, Polymethyl methacrylate PMMA, a porous membrane, or UV curable resin.

The polymer is optically transparent material that enables beam that excites the temperature sensitive fluorescent dye molecules to reach the inside effectively.

A Polyvinylidene fluoride PVDF membrane or a Nitrocellulose NC membrane, etc. is preferably used as a porous membrane.

A thickness of the porous film is in a range of 10 um to 0.1 mm is preferred.

A porous film is formed by spraying on the porous film after melting the temperature sensitive fluorescence dye in the polar solvent. The porous film is installed in the nucleic acid amplification chamber according to an embodiment of the present invention.

In an embodiment of the invention, collimator, for collecting the fluorescent light of the temperature sensitive fluorescent dye and sending it in an optical sensor direction, and the temperature sensitive polymer synthesis are installed together.

The collimator may be formed by any one of method selected from a depositing on the surface of the temperature sensitive polymer synthesis by a nitric acid reaction, directly coating on the surface of the temperature sensitive polymer synthesis by a sputtering process, and adhering a high reflectivity metallic film to on the surface of the temperature sensitive polymer synthesis.

To measure the fluorescent light of the temperature sensitive fluorescence dye, a filter is further included a front end of the optical sensor for blocking exciting lights and only passing emitted light is further included, according to an embodiment of the present invention, but is not limited thereto.

The optical sensor may further includes an optical cable, attaching the optical sensor to one end and placing the other side placed near the fluorescent light to measure the florescent light.

The fluorescent light of the temperature sensitive fluorescence dye may be replaced by a thermochromic ink such as a chameleon ink or thermocolor ink which the temperature sensitive fluorescence dye mixes a temperature sensitive pigment discoloring in the specific temperature according to an embodiment of the present invention, but is not limited thereto.

The thermochromic ink may be coated in the nucleic acid amplification chamber or a thermochromic ink coated porous film arranged in the nucleic acid amplification inside of chamber according to an embodiment of the present invention.

In this case, the disk is heated by the temperature controller, it has the property that the color of the thermochromic ink is changed at the predetermined temperature of in the liquid of the nucleic acid amplification chamber.

At this time, the laser beam is transmitted through the thermochromic ink and the optical sensor measures the light transmission amount in the opposite side.

A temperature of the liquid material can be measured since the light sensed through the optical sensor differs on intensity according to a color change of the thermochromic ink.

According to an embodiment of the present invention, the disk further includes one or more temperature sensor chambers on the disk for measuring a temperature of the ambient air.

The temperature sensor chamber is coated with a temperature sensitive polymer synthesis or integrated with thermochromic ink.

The temperature sensor chamber is in a concentric circle with the nucleic acid amplification chamber.

According to an embodiment of the present invention, a temperature measurement of the temperature sensitive fluorescence dye or the thermochromic ink is performed by an optical temperature sensor which includes a laser beam generator and an optical sensor.

According to an embodiment of the present invention, at least one air temperature sensor is arranged inside the case for measuring a temperature of the ambient air.

At least one of temperature sensors are arranged around the disk measure a temperature of the case inside with an average metrics of the temperature sensors or a weight average value of the temperature sensors.

The air temperature sensor may be used from any one of a thermocouple, a thermistor, and a laser temperature sensor.

According to an embodiment of the present invention, the optical sensor can be used from any one of a photo diode, the photodiode array, spectrometer, a charge-coupled device CCD, a Complementary metal CMOS, an image sensor, and a laser power meter.

The optical sensor includes a fluorescent filter that can measure an amount of fluorescent intensity emitted from the temperature sensitive fluorescent dye.

In another embodiment of the present, the optical sensor can be used as a fluorescent sensor to quantitatively analyze a fluorescent labeled nucleic acid amplification product.

According to an embodiment of the present invention, the disk, includes an azimuthal reference hole or a reference marker for supplying the information to the optical temperature sensor, for measuring a temperature of the nucleic acid amplification chamber in a real time while in rotation.

The azimuthal reference hole or the reference marker are located in the same radius as a radius of nucleic acid amplification chamber.

A bar code may be used as a reference marker according to an embodiment of the present invention.

Light transmission percentages caused by laser beam and optical sensor installed as transmission can differentiate reference hole based on light transmission percentage because the disk and azimuthal reference hole have different values, enabling Azimuthal space addressing of the nucleic acid amplification chamber taking in accord the reference hole and can distinguish and extract the temperature measurement signal of the nucleic acid amplification chamber in real time.

The barcode, printed on the disk, includes information which are a light penetrable and a non-penetrable areas.

The bar code can be used as a disk identification ID information in addition to be used as an azimuth angle information.

The azimuth reference hole or reference marker can distinguish and extract the temperature measurement signal of the nucleic acid amplification chamber in a real time, by light transmittance measurement by laser beam and optical sensor and enabling azimuth space addressing of nucleic acid amplification chamber while in rotation.

According to an embodiment of the present invention, a nucleic acid amplification is performed by repetitively performing a Polymer Chain Reaction amplification and a thermos cycle.

According to an embodiment of the present invention, the nucleic acid amplification is performed by an isothermal amplification.

Amplification is performed by repetitively performing a temperature cycle reaction including a denaturation about at 95° C., and an annealing about at 50° C. and an extension about at 72° C.

But the isothermal amplification is performed in the specific temperature, for example, about 60° C. for about 90 minute.

The amplification requires three different temperature control and requiring the nucleic acid amplification chamber to be coated by mixing 3 different thermochromic inks representing 3 different temperatures.

But in case the temperature sensitive fluorescence dye, one temperature sensitive fluorescence dye can represent 3 different temperatures by an emissive intensity property.

In case of the isothermal amplification, the nucleic acid amplification chamber inside the thermochromic ink of one temperature is coated. The emissive power measurement of the fluorescence dye in which the temperature sensitive fluorescence use of dyestuffs comes under the isothermal amplification since case shows the emissive power emission intensity property of the other fluorescence dye according to the temperature is instead of requisite with thermochromic ink.

The nucleic acid amplification disk case further includes an insulating material to insulate the external air.

The case includes an external wall side and the surface of inside wall covering thereof and the insulating materials in there between.

While exchanging 3 different temperatures in order to perform the amplification thermo cycle it is difficult to avoid an overshoot or an undershoot due to the reaction speed difference between an temperature inside wall surface of the case and air temperature of the case inside as the ambient temperature vary The undershoot or the overshoot or happens because the rate of change of the temperature of the inner surface wall of the case response slower than that of the inner air.

Therefore, According to an embodiment of the present invention, the case heater is installed between internal wall of the case surface and the external wall of the case to rapidly change the response speed of the temperature of the internal wall of the case.

To raise the temperature of the atmosphere of the case inside, the temperature controller and the case heater are operated at the same time.

The heating wire or a Positive Temperature Coefficient thermistor heating elements PTC is preferred as the case heater.

Moreover, the case further includes a case cooler installed between the internal wall of the case and the external wall of the case according to an embodiment.

One or more peltier element is installed between an internal wall of the case and an external wall of the case for heating or cooling the case.

It is suitable for the analysis equipment which nucleic acid amplification disk unit and the analysis method using the same of the present invention detect with immunology inspection using the bio-material inspection, food poisoning bacteria inspection, radioactive contamination inspection, meat kind and place of origin identification inspection, the gene variation foodstuffs inspection, and DNA, inspection of *bacillus* such as the disease inspection by the gene, and the colon *bacillus* and *Salmonella*, and inside of fluid DNA such as the ones real child confirmation, and the meat kind and place of origin identification inspection.

The DNA is selected from any one the Genomic, the Viral, and the Bacterial DNA is preferred.

Moreover, an inspection may be combined with at least any one of an immunology inspection, a residual antibiosis inspection, a residual agricultural medicines inspection, and food allergy inspection, and contaminant inspection.

The pesticide remnant is used to inspect most used organic phosphorus herbicide, carabmate based pesticides among the pesticides used on vegetables, greens, or fruits.

The bacteria a colon *bacillus*, a *pseudomonas* an *aeruginosa*, a *staphylococcus*, a *vibrio*, a salmonellae is preferred as the bacteria according to an embodiment of the present invention.

The radioactive contamination inspection inspects the change in the amount of gene with the radioactivity exposure according to an embodiment of the present invention.

The bio-material is selected from DNA, oligonucleotide, RNA, PNA, ligand, receptor, antigen, antibody, milk, urine, saliva, hair, crops and vegetable sample, and the meat sample, fishes sample, birds sample, the sewage, the polluted water, domestic animals sample, foodstuff, food sample, mouth cell, tissue sample, saliva, semen, protein, or biomass according to an embodiment of the present invention.

In the urine sample analysis, the nucleic acid amplification disk unit can perform leucocyte, blood, protein, nitrite, PH, specific gravity, glucose, ketone, ascorbic acid, urobilinogen, or bilirubin analysis.

It has the advantage of accurately measuring the historical record by the accumulation of the nutriments of body including mineral and toxic material in the hair sample in comparison with blood or the catch urinalysis.

It accurately can figure out an excess and lack of a long-term inorganic material and an amount of toxic heavy metals.

The foodstuff etc. are referred to including more specifically, the foodstuff for the pot stew the equation material refers to the material for cooking, the foodstuff for the spaghetti and noodles, the foodstuff for making the Kimchi, the foodstuff for making the bureau to the tang, and soup.

The remnant chamber is positioned at the more outside than the centrifugation chamber from the center of the nucleic acid amplification disk.

According to an embodiment of the present invention, the isolation channel is further included between a remnant chamber and a centrifugation chamber.

It is separated into the blood serum and blood clot to plasma and red blood cell if blood is centrifuged separation. The red blood cell occupies the majority of the blood clot.

Therefore, the blood serum remained in the centrifugation chamber if blood is centrifuged. The red blood cell is remained in the remnant chamber. The red blood cell is again mixed with the blood serum if the rotation is stopped. That is, the rotation of the disk has to be stopped to take off only the blood serum after the centrifugation, the red blood cell and blood serum are again mixed thus, and it is difficult for taking off the blood serum.

In order solve this problem, the isolation channel is arranged between the remnant chamber and the centrifugation chamber. Due to a capillary phenomenon and a strong connectivity between a surface of remnant chamber and the red blood cell, the red blood cell does not get mixed with the blood serum and remains behind in the remnant chamber.

When the rotation stops, binding force between the surface of remnant chamber and the red blood cell caused by the high viscosity prevents the centrifuged red blood cell from remixing with the serum and allows it to remain in the remnant chamber.

The nucleic acid amplification disk may include functions for storing and transmitting of reading result about the nucleic acid amplification product and/or the radio frequency RF and integrated circuit IC having the individual password function.

The driving controller may include a detector for detecting a nucleic acid amplification product in a real time and an optical sensor may be as the detector.

The disk may further includes a valve or a thin film cylinder magnet for searching an azimuthal direction of the preparation chamber.

Instead of the thin film cylinder magnet, a thin film ferromagnetic substance metal particle can be used.

A diameter and a thickness of the thin film ferromagnetic substance metal particle and thin film cylinder magnet is in a range of 1 mm to 5 mm and 0.1 mm to 1 mm, respectively.

According to an embodiment of the present invention, preferably, a hydrophilicity fluid path is formed with a porous surface by the surface modification or an aqueous paint or the hydrophilicity paint coating.

A driving controller includes a slider which can move in a radial direction, a slide motor which can control the movement of the slider.

A laser beam generator and per permanent magnet is mounted on the slider

According to an embodiment of the present invention, preferably, the space addressing of the disk is performed by a radial direction search and an azimuthal direction search, the radial direction search is performed by the slider motor, and with stopping the slider, the azimuthal direction search is performed by rotating the disk a predetermined amount with short turn controlling of the spindle motor or controlling stepping motor.

The rotation of the disk any more does not occur for the short rotation of the spindle motor between the permanent magnet and the thin film cylinder magnet with an attractive force and stops and the azimuth search is performed at the thin film cylinder magnet location.

The stepping motor may be connected on the spindle motor shaft with a gear for rotating in an azimuthal direction of the body.

The driving controller controls each laser module corresponds to the valve for independently opening and closing each valve, the each laser module is arranged to each valve each laser module based on the space addressing of the preparation chamber.

The driving controller may control the light illumination heater to locally heat the nucleic acid amplification chamber after azimuth direction search of nucleic acid amplification chamber by the stepping motor rotation.

According to an embodiment of the present invention, preferably, to increase a washing efficiency of the magnetic bead, space addressing of the preparation chamber for the washing process, and inducing a movement of the magnetic bead with an attractive force between the permanent magnet on the slider and the magnetic bead by rotation of the disk or a short repetition movement the slider are provided.

A material of disk may be selected from the various materials such as a plastic, a glass, a silicon wafer, a hydrophobicity material, etc.

Preferably, the disk is formed of one or more materials selected from the group consisting of silicon wafer, polypropylene, polyacrylate, polyvinyl alcohol, polyethylene, polymethyl methacrylate PMMA, the cyclic olefin polymer cyclic olefin copolymer COC: and polycarbonate.

Moreover, the disk can be coated with aluminum to prevent from evaporation of a liquid in which the disk is stored in chamber. The disk may include an upper substrate, an intermediate substrate, and a lower substrate which are multilayered by an adhesive.

The adhesive is made of a material selected from the group consisting of a silicone, a rubber, a modified silicon, an acryl acrylic, polyester, and epoxy materials.

The body includes a upper substrate, an intermediate substrate, and a lower substrate are multi-layered bonded, and may further includes a first double sided adhesive tape in between the upper and the intermediate substrate, and a second double sided adhesive tape is in between the intermediate substrate and the lower substrate for multilayered-bonding.

The double-sided adhesive tape is surface-treated in both side surface of the release paper by a special adhesive such as a paper, vinyl, polyester film, polyethylene film and the other composite.

According to the condition needed, the adhesive material may be selected materials from characteristic of high sealing, a sealing shock-absorbing, vibrational relaxation, an impact resistance, a heat resistance, an adsorption capability, an adhesive force, etc.

In another embodiment of the invention, the double sided adhesive tape does not use a lease paper or backing, but an adhesive or a gluing agent itself forms the double sided adhesive.

The double-sided adhesive tape is adhesive is coated on the both side of a release paper or adhesive itself forms.

The material like hot melt, silicone, rubber, modified silicon system, acryl group acrylic, polyamide, polyolefin, Teflon-like, polyester, epoxy, an ultraviolet ray sense curing resin UV curable adhesive, UV adhesive, a thermoplastic resin, etc. may be used as adhesive material.

A COC, PE, PMMA, PC, PS, POM, PFA, PVC, PP, PET, PEEK, polyamide PA, PSU and PVDF are preferred as a thermoplastic resin.

It is preferred that the adhesive is melted with a heat of the laser beam. A fluid hole is closed by the adhesive when the substrate bonding. The valve is opened when the adhesive around the fluid hole is fused with the heat of the laser beam.

The hot melt tape or the thermoplastic tape has a melting property when heated with the laser beam.

The tape channel is further formed by the double-sided adhesive tape in which the flow path shape is formed between the layers of the substrates according to an embodiment of the present invention.

That is, the substrates 1, 2, 3 are bonded by the double sided adhesive tape forming a disk, the tape channel is formed between the substrates where the double sided adhesive tape is missing.

A height of the fluid path of the tape channel is determined by a thickness of the double-sided adhesive tape and generally the height is very low and therefore strong capillary tube are formed at the fluid path according to an embodiment of the present invention, the thickness of the double-sided adhesive tape is in a range of 0.001 mm to 0.1 mm.

Effects of the Invention

Embodiments of the present provide a nucleic acid amplification disk apparatus using a temperature sensitive polymer synthesis and the analysis method using the same, more specifically, the embodiment provide all kinds of the diagnosis analysis equipment, the nucleic acid amplification disk apparatus which is for the Genomic necessary for the nucleic acid hybridization assay apparatus or the immunologic verifying device, the Viral, and the Bacterial DNA or RNA to more easily efficiently amplify and automatizes the fabrication of relating to the nucleic acid amplification, and the analysis method using these.

DESCRIPTION OF EMBODIMENTS

Figure 1A:
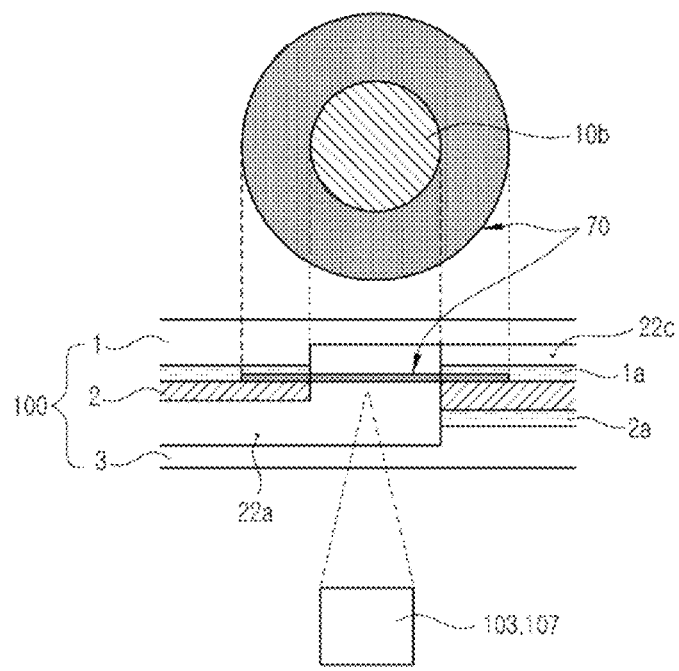
FIG. 1A is a cross-sectional view of the laser burst valve necessary for the nucleic acid amplification disk according to an embodiment of the present invention FIG. 1B_A, FIG. 1B_B, FIG. 1C_A and FIG. 1C_B show a nucleic acid amplification disk in which the nucleic acid amplification process are arranged.

The above and other aspects, features, and advantages of certain exemplary embodiments of the present invention will be more apparent from the following description taken in conjunction with the accompanying drawings, in which:

FIG. 1A is a cross-sectional view showing the laser burst valve necessary for the nucleic acid amplification disk according to an embodiment of the present invention.

A valve for controlling a flow or a flow rate of a fluid used for the nucleic acid amplification process being installed on the nucleic acid amplification disk, includes a laser burst valve, including a thin film 70 on the fluid hole area 10b, which is opened, defused or teared by a heat of a laser, The laser burst valve independently controls opening and/or closing a plurality of fluid whole 10b installed on the disk 100.

A diameter and a thickness of a film are in a range of 1 mm to 5 mm and 0.001 mm to 0.2 mm, respectively.

Membrane formed from black film, vinyl or black paint absorbs the emitted light energy from laser module apparatus 103 and can easily melt or tear even at a low laser power.

The nucleic acid amplification disk 100 includes an upper portion substrate 1, an intermediate substrate 2, and a lower substrate 3, a fluid path i.e. channel for flowing a fluid while an injection molding process, a chamber for storing a buffer solution, and a plurality of fluid hole for connecting the fluid path. These are adherently bonded to be a single disk 100.

The disk 100 may include a first double-sided adhesive tape 1a arranged between the upper substrate 1 and intermediate substrate 2 for bonding thereof and a second double-sided adhesive tape 2a arranged between the intermediate substrate and the lower substrate for bonding thereof.

FIG. 1A shows a fluid hole 10b is blocked by the film closing the fluid paths 22a 22c and the laser module device 103 is turned on to melt the film 70 and to open the fluid hole 10b thereby opening the fluid paths 22a 22c.

The first double-sided adhesive tape 1a is served as the film 70. In this case, it is preferred that the double-sided adhesive tape 1a is coated by the adhesive on the both side surface of the black body release paper The black body release paper and the film 70 is any one of selected from the poly ethylene PE, a polypropylene PP, and a polyvinyl chloride PVC are preferred.

The film is a black film is preferred according to an embodiment of the present invention.

In an embodiment of the present invention, the black film is formed by printing the fluid hole area 10b the first double sided adhesive tape 1a with blackbody ink The collimated laser beam is focused on the film 70. Therefore, According to an embodiment of the present invention, the lower substrate 3 of the upper substrate 10b has convex lens shape, Convex lens of both sides or hemisphere can be used as the convex lens shape when the discs is injection molded, the convex lens designs thin film membrane 10b area of the lower substrate 3 to have convex lens shape.

Therefore, the upper portion substrate 1 of the fluid hole 10b further includes a reflective film (i.e. Reflector).

The upper portion substrate 1 may further include a reflective film or a reflector at the fluid hole.

Paraffin wax, synthetic wax, microcrystalline wax are preferred as a black body ink.

An adhesive of the black film absorbs energy from the laser beam in the adhesive and heats and prints a plurality of micro heating particles to be formed on the fluid hole 10b or around the fluid hole 10b.

A plurality of micro heating particles are heated to fuse the adhesive by an illumination of the laser beam.

The micro heating particle is a particle selected from any one of a ferromagnetic substance, a magnetic fluid or the metal oxide the minute heating particle.

An embodiment of the present invention, the black body ink is made of mixing micro heating particles.

The ferromagnetic powder called the magnetic fluid is the ultrafine particles in a range of 1 nm to 100 nm is utilized.

The liquid of the colloid state has magnetism using the surfactant like the fatty acid.

It is preferred to be the ferromagnetic is at least one selected from group consisting of Fe, Ni, and Cr and the oxide thereof.

The metal oxide is selected from group consisting of Al2O3, TiO2, Ta2O3, Fe2O3, Fe3O4, and HfO2.

An embodiment of the present invention, the laser beam generator 107 mounted on a slider is space addressed at the predetermined valve and generates a beam for opening the predetermined valve.

FIGS. 1B_A-1C_B show embodiments of the nucleic acid amplification disk in which the nucleic acid amplification process of amplifying DNA from the DNA sample is arranged.

FIG. 1B_A and FIG. 1B_B show that only one nucleic acid amplification chamber 52a is provided, whereas FIG. 1C_A and FIG. 1C_B show that two nucleic acid amplification chambers 52a, 52b are provided according to an embodiment of the present invention.

A DNA sample chamber 25 stores DNA samples for temporarily, to be amplified, acquired through the DNA inlet port 26. The DNA samples moves to the nucleic acid amplification chamber 52a 52b through the sample movement channel 40 during the disk rotation. After filling the necessary amount of DNA samples to the nucleic acid amplification chamber 52a 52b for nucleic acid amplification reaction. Any surplus DNA samples moves to the trash chamber 23 through an overflow channel 47.

However, when the nuclei acid amplification chamber 52a 5b heats for the nucleic acid amplification reaction, it is hard to acquire trust worthy nucleic acid amplification result because liquefied DNA samples will evaporate vigorously and move part of DNA samples to surrounding area through the sample movement channel 40 and the overflow channel 47.

According to an embodiment of the present invention, a Phase change material (PCM) door including PCM chambers 50a 50b 50c and capillary channels 53a 53b 53c is provided to prevent it.

Phase change material (PCM) 54 is saved in the PCM chambers 50a 50b 50c. Before heating the nucleic acid amplification chambers 52a 52b, a solid state PCM 54 is liquefied by using the heat of laser beam generator 107 and filling to the sample movement channel 40 and the overflow channel 47 through the capillary channels 53a 53b 53c by capillary phenomenon or centrifugal force.

By stopping the heating, the PCM 54 turns back into solid state sealing the sample movement channel 40 and the overflow channel 47.

This way, nucleic acid amplification chambers 52a, 52b are blocked from the DNA sample chamber 25 and trash chamber 23 and preventing loss of the liquid in nucleic acid amplification chambers 52a, 52b during heating of nucleic acid amplification chambers 52a, 52b.

FIG. 1B_A shows that the sample movement channel 40 and the overflow channel 47 before they are sealed.

FIG. 1B_B shows that is the channel 40 and the overflow channel 47 after they are sealed. The internal surface of PCM chambers 50a 50b 50c are coated with a black body.

FIG. 1C_A shows that a nuclei acid amplification disk 100 with two nuclei acid amplification chambers 52a 52b. In this example, a variety of DNA amplification for single sample are possible because different primers are used in the each nucleic acid amplification chamber 52a 52b.

FIG. 1C_B shows that the nuclei acid amplification disk 100 may include two independent nuclei acid amplification processes. In this example, a variety of DNA amplifications for single sample are possible because different primers are used for each nucleic acid amplification chambers 52a 52b.

Figure 2:
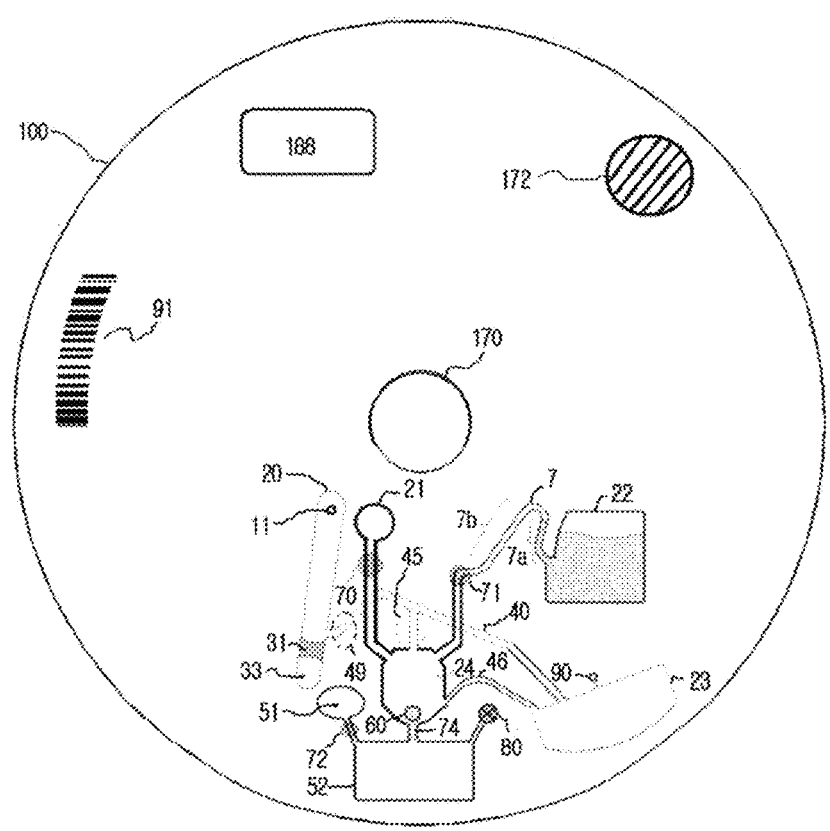
FIG. 2 shows a process of amplifying DNA from the DNA sample is arranged

FIG. 2 shows that nuclei acid amplification processes are collectively arranged on a nuclei acid amplification disk 100.

Figure 3A:
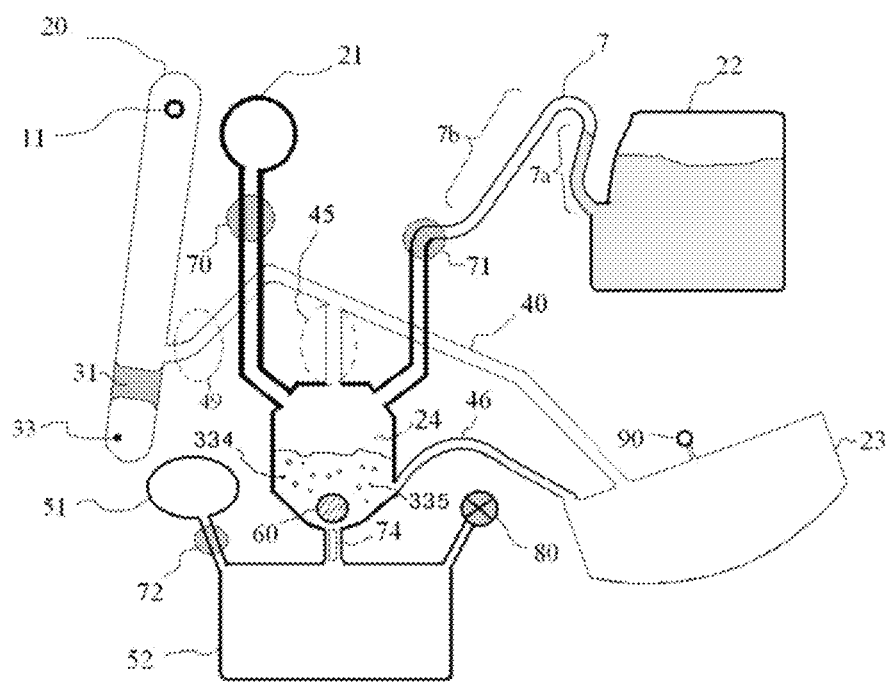
FIG. 3A shows a detail view of the nucleic acid amplification disk in which the nucleic acid amplification process are arranged.

FIG. 3A shows detailed drawings of the FIG. 2.

Figure 3B:
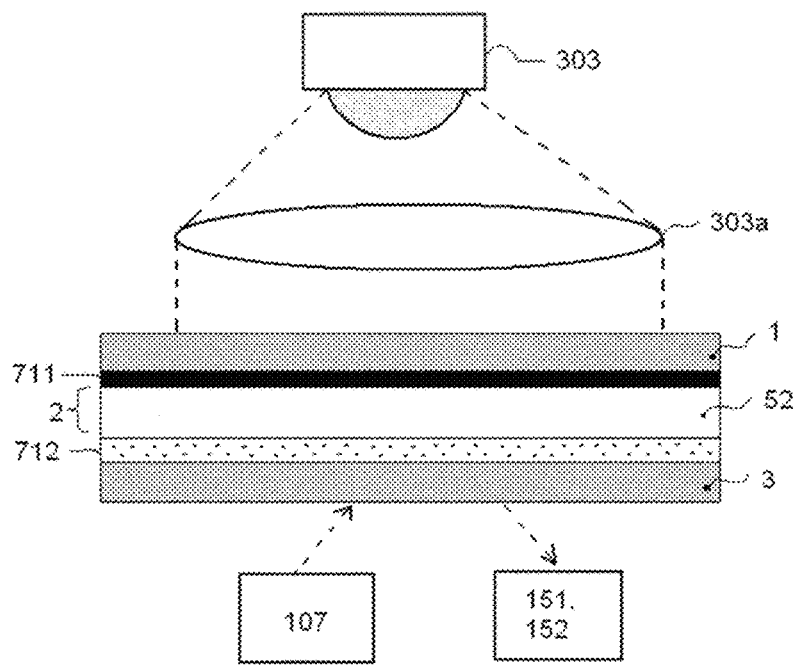
FIGS. 3B-3C show a light illumination heater heating a nucleic acid amplification chamber

More specifically, FIGS. 2, 3A, and 3B shows that the nucleic acid amplification disk 100 includes a sample inlet port 11 for injecting the sample, a centrifugal chamber 20 for removing remnant from the clinical sample to obtain sample or separating whole blood plasma from the whole blood by centrifugation while storing the sample, a remnant chamber 33 for storing a remnant, a washing chamber 22 for storing a washing buffer, a preparation chamber 24 for lysising a cell in the sample, separating refined DNA and RNA, which debris removed in the washing buffer, and preparing DNA sample from RNA by a reverse transcription (R-T), a nucleic acid amplification chamber 52 for storing the buffer solution and all kinds of the enzymes needed for nucleic acid amplification and for performing nucleic acid amplification, and a fluid path or channel for connecting chambers thus allowing fluid flowing among chambers according to an embodiment of the present invention.

A disk air gap 170 and a metering chamber 45 supplies predetermined sample to the preparation chamber 24.

Detainment channel 49 detains sample in a centrifugal chamber 20 for centrifugation of the disk and is located between the centrifugal chamber 20 and the sample movement channel 40.

If the whole blood using anticogent is used as a clinical sample and centrifuged, a plasma, a white blood cell platelet and a red blood cell are separated starting in an order of low specific gravity. The sample detainment cannel 49 controls the height of the centrifugation separation chamber 20 to accept the white blood cells first because DNA is included in the white blood cells.

When the rotation of disk 100 pauses, firstly, the white blood cell fills the metering chamber 45 providing the white blood cell to the preparation chamber 24 by hydrophilicity and capillary tube fluid movement. According to an embodiment of the present invention, the sample movement channel 40 and metering channel 45 are hydrophilicity coated. The sample moving to the sample movement channel 40 moves to the trash chamber 23 by the disk rotation while the sample in the metering chamber 45 moves to the preparation chamber 24.

According to an embodiment of the present invention, the sample movement channel 40 and the metering channel 45 forms a T shape and the sample in the sample movement channel 40 is moved to the trash chamber 23 by the first centrifugal force while remaining predetermined amount of sample in the metering channel 45 during the disk rotation.

Samples in the metering chamber 45 is moved to the preparation chamber 24 by the second centrifugal force that has a high disk rotation speed. Therefore, the second centrifugal force demands higher rotating speed of the disk in comparison with the first centrifugal force.

The disk rotation speed for the first centrifugal force is in a range of 200 to 600 rpm, and the rotation speed of the disk for the second centrifugal force is in a range of 600 rpm to 2000 rpm according to an embodiment of the present invention, however, it is not limited thereto.

According to an embodiment of the present invention, a lysis buffer 334 for lysising a cell, and a magnetic bead 335 that combines with an exposed DNA are in the preparation chamber 24 to disassemble the cells. Washing is needed to remove impurities created during the cell lysising process.

Therefore, a neodymium magnet 60 is in the preparation chamber 24 to have the magnetic bead 335 remained in the preparation chamber 24 during the washing process and only impurities be moved to the trash chamber 23.

During the washing process, the magnetic bead 335 remained in the preparation chamber 24 due to strong magnetic force between the magnetic bead and a neodymium magnet 60.

The washing process is performed repeatedly 2-3 times by supplying the washing buffer in the washing chamber 22 to the preparation chamber 24 and sequentially washing the magnetic beads and moving only impurities through the check channel 46 to the trash chamber 23, however it is not limited thereto.

After the washing buffer valve 71 is opened, the washing buffer is provided from the washing chamber 22 through the pump channel 7.

According to an embodiment of the present invention, a pump channel 7 is hydrophilic coated, and the washing solution is repetitively supplied to the preparation chamber 24 by hydrophilic and capillary effect caused by the rotation and pause of the disk 100.

During the rotation of the disk 100, a first pump arm 7a of pump channel 7 restrains washing liquid and when the rotation is paused, a first pump arm 7a and a second pump arm 7b are filled with the washing liquid by hydrophilic fluid and capillary phenomenon, and when the rotation begins again, the washing fluid in pump arm 27b moves to the preparation chamber 24 and washes the magnetic bead 335.

The check channel 46 is hydrophilic coated. While the disk 100 is rotating in a reverse "V" shape, impurities remain in the preparation chamber 24, and when the disk 100 stops rotating, impurities move to the trash chamber 23 through the check channel 46.

The check channel 46, the pump channel 7 and the sample movement channel 40 are in a reverse "V" shape.

The elution of DNA attached to the magnetic bead 335 in the preparation chamber 24 is performed by supplying the resuspension buffer or the elution buffer in the elution buffer chamber 21 to the preparation chamber 24.

Specifically, the elution of DNA occurs at a predetermined time by opening the DNA movement control valve 80 after the opening of valve 70 and supplying resuspension buffer or elution buffer to the preparation chamber 24 by the rotation of the disk 100.

DNA deviated by the elution buffer of the magnetic bead 335 moves to the nucleic acid amplification chamber 52 with the centrifugal force caused by the disk rotation through the DNA movement channel 74. The DNA movement to the nucleic acid amplification chamber 52 by the centrifugal force occurs after the DNA movement control valve 80 opens. While the magnetic bead 335 in the preparation chamber 24 is washed, the role of the DNA movement control valve 80 is to prevent any fluid movement to the nucleic acid amplification chamber 52. This role is continued until DNA is separated from the magnetic bead 335 with the elution buffer.

Because there is no exhaust pipe in the nucleic acid amplification chamber 52, when the DNA movement control valve 80 is closed, the DNA movement to the nucleic acid amplification chamber 52 from the preparation chamber 24 does not occur under an appropriately controlled centrifugal force condition.

DNA extracted from the magnetic bead 335 is moved to the nucleic acid amplification chamber 52 after opening the movement control valve 80 by the rotation of the disk 100.

The magnetic bead 335 remains in the preparation chamber 24 because of the neodymium magnet 60. The DNA movement channel 74 is formed with a tape channel. In this case, a backward flow of the fluid in the nucleic acid amplification chamber into the preparation chamber 24 caused by the strong capillary effect is prevented. In another embodiment of the invention, the DNA movement channel 74 is composed of a laser burst valve instead of a tape channel.

In this case, after the DNA movement channel 74 is opened with the laser beam, a DNA in the preparation chamber 24 is moved to the nucleic acid amplification chamber 52 with the strong rotation of the disk. Then the valve 72 is opened and the polymerase stored in the polymerase chamber 51 is moved to the nucleic acid amplification chamber 52.

A nucleic acid amplification chamber 52 stores a buffer solution including all kinds of the enzymes, primer including the dNTP. After, heating or amplification thermocycle for isothermal amplification can amplify the DNA. The reference numeral 90 is the exhaust pipe.

An isolation channel 32 isolates samples in the centrifugal separation chamber 20 from the remnant. According to an embodiment of the present invention, a tape channel may include the isolation channel 31 and the DNA movement channel 74.

The tape channel is formed in the disk assembly by inserting and arranging the first double-sided adhesive tape 1a and the second double-sided adhesive tape 2a in the center of the remnant chamber 33 and the centrifugation chamber 20.

An isolation channel 31, formed with the tape channel, can stop re-movement of a remnant of remnant chamber 33 to the centrifugal separation chamber 20 while the disk is paused.

When disk is paused, it is impossible for the remnant in the remnant chamber 33 created by the strong capillary tube in the isolation channel 31 to move freely to the centrifugal separation chamber 20 or sample detainment channel 49

At the start and the end of each process preparation process, the nucleic acid amplification process, the valve opening and closing may be controlled by the laser beam on and off control of the laser module 103 and centrifugal force by the rotation of the disk causes the fluid movement.

A wireless RF IC 188 stores personal encryption information and cannot be used by other.

A bar code 91 provides a reference marker or a product identification (ID) of the disk.

The barcode includes disk's product ID, expiration date, and information regarding types of disease for analysis and diagnose.

The bar code can be read with the laser module 103 or the laser beam generator 107.

According to an embodiment of the present invention, the thin film cylinder magnet for the azimuthal direction search is achieved through the neodymium magnet 60.

A temperature sensor chamber 172 is coated with the temperature sensitive polymer synthesis. The temperature of an ambient air can be measured by measuring the fluorescent intensity from the polymer synthesis with the laser beam generator and/or the optical sensor.

The lower substrate 3 of the nucleic acid amplification chamber 52 is coated with the temperature sensitive polymer synthesis, the temperature of the liquid in the nucleic acid amplification chamber 52 can be measured by measuring an intensity from the temperature sensitive polymer synthesis by the optical sensor.

FIG. 3B shows the lighting radiation heater heats the nucleic acid amplification chamber 52 according to an embodiment of the present invention.

For absorbing a heat from the lighting radiation heater 303 and heating up the nucleic acid amplification chamber 52, a black film or the black paint coating layer 711 is arranged between the upper substrate 1 and intermediate substrate 2.

A collimator 303a is to collimate a collimated light emitted from the light illumination heater 303.

The temperature sensitive polymer synthesis 712 is coated on the upper side of the lower substrate 3 of the nucleic acid amplification chamber 52 to measure the temperature of the liquid material with in the chamber.

A laser beam of the laser beam generator 107 passing through the lower substrate 3 excites the fluorescent material in the temperature sensitive polymer synthesis 712. The fluorescent quantity from fluorescent material can be measured with the optical sensor 151 or the fluorescent sensor 152. Accordingly, a feedback control of the laser beam generator 107 can be performed using the sensed output.

Pulse Width Modulation (PWM) control is mask pattern with heat blocking ability is installed between the light illumination heater 303 and nucleic acid amplification chamber 52 by on/off time of mask pattern.

Figure 3C:
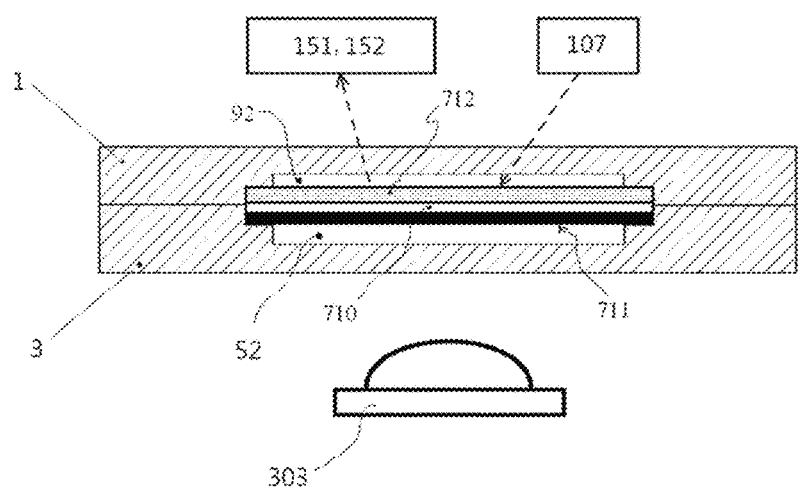

FIG. 3C shows the lighting radiation heater 303 heats the nucleic acid amplification chamber 52 according to another embodiment of the present invention.

Between the upper substrate 1 and the lower substrate 3, the black film or the black paint coated layer 711 for absorbing heat from the lighting radiation heater 303 and heating the nucleic acid amplification chamber 52, a temperature sensitive polymer synthesis layer 712, and the collimator 710 for collimating the fluorescent light generated temperature sensitive polymer synthesis 712 to the optical sensor 151 or the fluorescent sensor 152 are arranged.

According to an embodiment of the present invention, the temperature sensitive polymer synthesis 712 includes temperature sensitive dye is coated on the porous membrane.

The black paint coating layer 711 and the collimator 710 are formed by coating one side of the metallic film or the aluminum foil at the same time according to an embodiment of the present invention. However, it is not limited thereto. Preferably, a thickness of the metallic film or the aluminum foil is in a range of 1 um to 100 um.

Heat generated from the light illumination heater 303 is absorbed by the black film or the black paint coating layer 711 and is transferred to the temperature sensitive polymer 712 through the collimator 710 while heating the sample filled in nucleic acid amplification chamber 52.

The air layer 92 is for preventing error of the temperature measurement losing the thermal energy when the temperature sensitive polymer synthesis 712 is in contact with the upper substrate 1.

Figure 4:
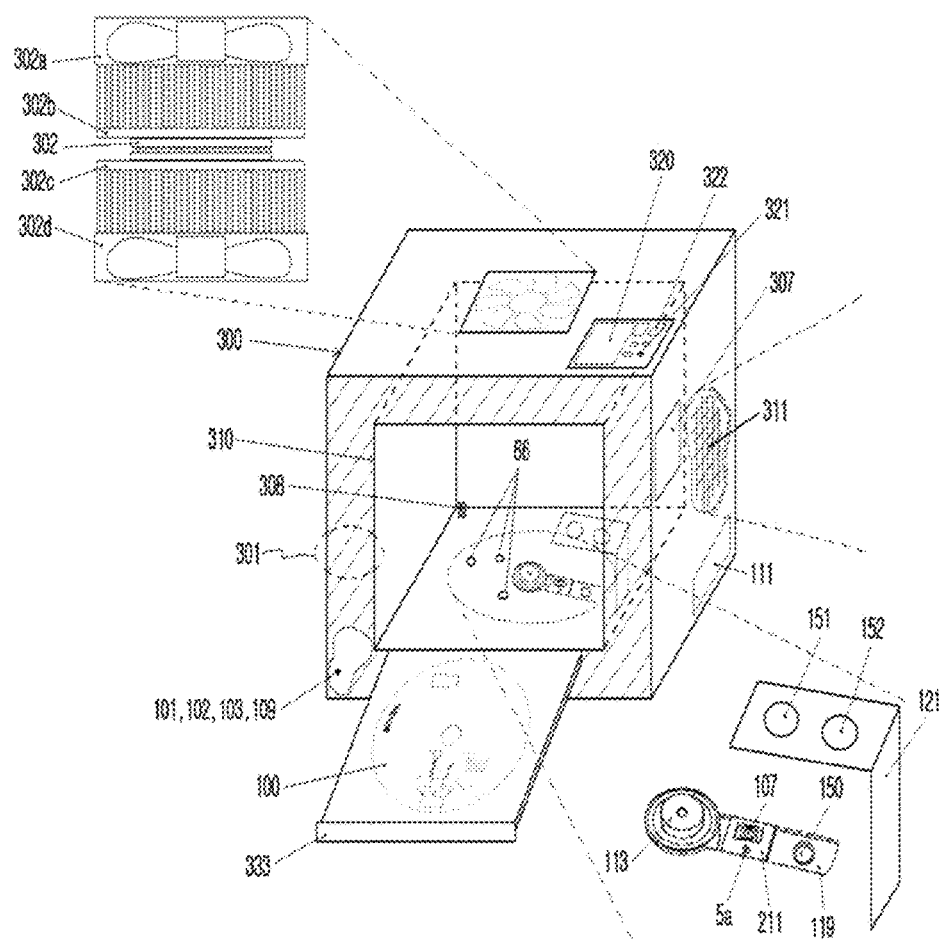
FIG. 4 shows outside of the nucleic acid amplification apparatus

FIG. 4 shows the Peltier element 302 is used for a temperature controller according to an embodiment of the present invention. A case 211 includes an external wall side 300 and an internal wall side 310 of the amplifying apparatus 311. The insulating material 301 is fill up in there between an external wall side 300 and an internal wall side 310 of the amplifying apparatus 311 of the amplifying apparatus the tray 333 is for loading the nucleic acid amplification disk 100 on the turn-table 113. The case external wall side 300 may include the display unit 320 for displaying the nucleic acid amplification progress, the power on/off button 322, and the button input part 321 for establishing the nucleic acid amplification time and the amplification thermo cycle.

The Peltier element 302 may further include the internal circulation fan 302*d*, the internal heat sink 302*c*, the external radiation plate 302*b*, and the external fan 302*a*.

The peltier element 302, as a type of heat pump, can be used by applying voltage and depending on the direction of the applied voltage, one side becomes cold and the other side becomes hot.

In an embodiment of the present invention, the both sides of peltier element 302 need to exchange heat with the atmosphere effectively because the amplification thermo cycle includes both heating and cooling.

Therefore, a heat exchange with the external atmosphere uses the outside heat radiation plate 302*b* and an external fan 302*a*; the heat exchange with internal atmosphere of case 301 uses internal heat radiation plate 302*c* and internal ventilation fan 302*d*.

The internal ventilation fan 302*d* aids to reach uniform temperature distribution in short amount of time by increasing heat exchange of internal atmosphere and circulation of internal atmosphere with vigor. Moreover, an air temperature sensor 308 is for measuring the temperature of inside of the case.

The sensor supporter 121 may mount both the optical sensor 151 and the fluorescent sensor 152 for measuring a fluorescent intensity emitted from the fluorescent material in the nucleic acid amplification chamber 52.

An optical sensor is installed on the sensor supporter 121 to form a transmission arrangement with the laser beam generator 107.

The laser beam generator 107 and the optical sensor 151 are disposed to be arranged in a row about an optical axis and include an optical temperature sensor for measuring the fluorescent intensity of the temperature sensitive fluorescence dye coated in the nucleic acid amplification chamber 52.

The laser beam generator 107 and optical sensor 151 are disposed to be arranged in a row about the optical axis and include an air temperature sensor for measuring the fluorescent intensity of the temperature sensitive fluorescence dye in the temperature sensor chamber 172.

The light source 150 and the optical sensor 152 are disposed to be arranged in a row about the optical axis and may be used for quantitatively analyzing the nucleic acid amplification product in the nucleic acid amplification chamber 52 through the fluorescence analysis.

The laser beam generator 107 and the optical sensor 151 may be modified for used as the reflective structure.

The light source 150 and the optical sensor 152 may be modified for used as a reflective structure according to an embodiment of the present invention.

By the space addressing, a laser beam generator 107 and a permanent magnet 5*a* on the slider 211 may access the nucleic acid implication disk 100 through an opening and closing hole 119.

The laser beam generator 107 can be used for the light radiation heater for heating the liquid in the nucleic acid amplification chamber 52 which includes the black film or the black paint coating side on the top substrate thereof.

The black film or the black paint coating side indirectly heat a liquid in the nucleic acid amplification chamber 52 by absorbs heat from the laser beam generator 107.

The thickness of the black film or the black paint coating side is in a range of 10 um to 100 um according to an embodiment of the present invention.

Laser holes 66, space addressing reference for the thin film cylinder magnet 60, one to one corresponds to the valve and each laser module 103 is arranged in the case 300 to independently control the opening and closing of each valve 70, 71, 72, 74, 80 for the laser beam to pass through the case inner wall 310. Here, a film 70 is a selective opening and closing, thus a type of valve, a DNA movement channel 74 is also a selective opening closing, thus, 71, 72, and 80 are also valves.

Moreover, a driving controller includes the central controller 101 for controlling a part of the nucleic acid amplification apparatus, the slide motor 109, the stepping motor 102 for rotating the nucleic acid amplification disk 100 and the laser module 103 are accommodated between the case external wall side 300 and surface of inside wall 310, however, it is not limited thereto.

Moreover, the nucleic acid amplification apparatus includes the external I/O device 111 which permits a connection with a computer or the internet network and allows transmission and/or reception about nucleic acid amplification result data of the amplifying apparatus and remote control using the internet network. Moreover, the nucleic acid amplification apparatus allows the access of the graphic user interface of the computer through the connection with the computer through the external I/O device 111. A progress of a major process, such as the preparation process, and the nucleic acid amplification process, may be displayed on the display unit 320 to the graphic user interface in a form of the percent (%) or the bar graph.

Moreover, fluorescence analysis result of the nucleic acid amplification may be displayed on the display unit 320 or the graphic user interface in a real time.

FIG. 4 shows a nucleic acid amplification, according to an embodiment of the present invention, which is a front loading mode of the nucleic acid amplification disk 100, however, it is not limited to be a top loading mode.

Figure 5:
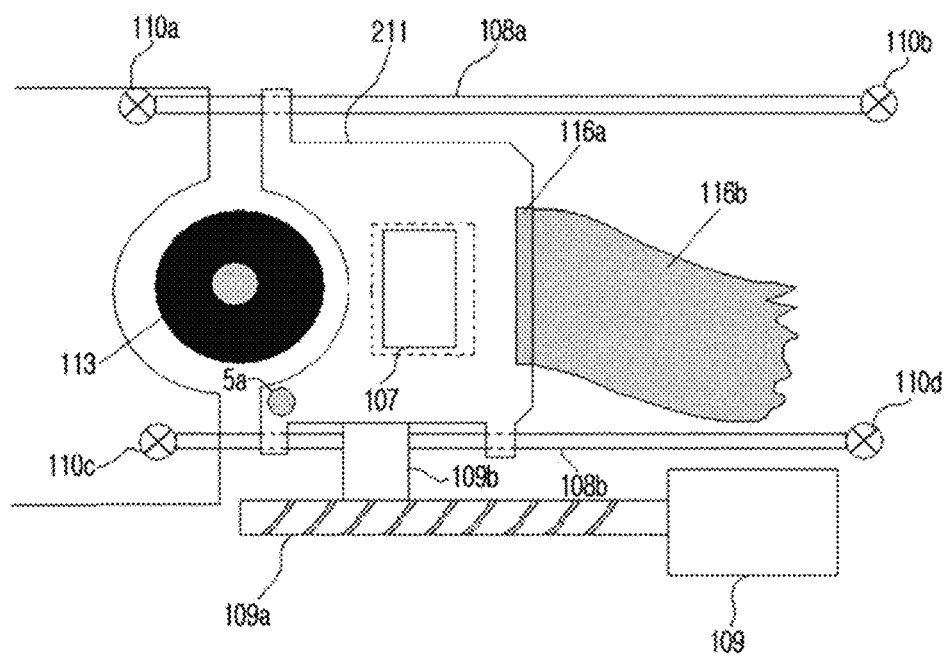
FIG. 5 shows a top view of the slider a permanent magnet is mounted on, and FIG. 6 shows a side view of driving controller for driving and controlling the nucleic acid amplification disk of FIG. 2.

FIG. 5 is a top view of the permanent magnet 5a is on the slider 211 according to an embodiment of the present invention, the slider 211 is moved and controlled by worm gear connection parts which is connected to the slide motor 109 shaft.

The slider slides using slide arms 108a, 108b as the guide. Slide arms 108a, 108b are connected to the body of the driving controller through screws 110a, 110b, and 110c, 110d the flexible cable 116b is connected through the wafer or the harness 116a. The stepping motor rotates a turn-table 113.

According to an embodiment of the present invention, the laser beam generator 107 may operate as any one of the light source for opening the valve, light illumination heater for heating liquid in the nucleic acid amplification chamber, or the heat source for exciting the fluorescent material for quantitatively analyzing the nucleic acid amplification product.

According to an embodiment of the present invention, the slider 211 may further include an optical sensor for detecting an opening or closing of the valve by the light quantity, a temperature sensor for measuring the temperature of the liquid in the nucleic acid amplification chamber 52 by a fluorescent intensity measurement, and a fluorescent sensor for quantitatively analyzing the nucleic acid amplification product in the nucleic acid amplification chamber 52 with the fluorescent intensity measurement.

FIG. 6 is a side view of a driving controller for controlling and driving the nucleic acid amplification disk 100 of FIG. 2 according to an embodiment of the present invention. A body 350 is for supporting the driving controller, the circuit board 140 on the bottom portion of the driving controller is connected the body 350 of the driving controller.

The central controller 101 for controlling the driving controller, the storage unit 112, and I/O unit 111 are installed on the circuit board 140.

The central controller 101 controls the stepping motor 102 for the rotation of the disk 100, controls the slide motor 109 control on the slider 211 for a movement of the laser beam generator 107.

In addition, the control controller 101 moves the permanent magnet 5a for space addressing for the preparation chamber 24 and valves of the disk 100. The permanent magnet 5a uses gravitational attraction effectively on the thin film cylinder magnet 60.

Moreover, the central controller 101 may control the slide motor 109, a stepping motor 102, a temperature controller 302, a case heater 307, a display unit 320, and a button input unit 321 and process information from. An air temperature sensor 308, the optical sensor 151, and a fluorescent sensor 152.

The temperature controller is selected among the combination of a peltier device, a compressor and a radiator, a heater or light illumination heater including a heating coil and a ventilation fan, an ultrasound heater, an illumination lamp; however, combination of peltier device and optical illumination heater is preferred.

The temperature controller is preferred among the Peltier device, the combination of the radiator and compressor, the heating coil and blower, the ultrasonic heating apparatus, and the combination of the heater by the luminescence lamp to the light examination heating apparatus with one or greater. But the combination of the light examination heating apparatus and Peltier element is more preferred, however, it is not limited thereto.

The Peltier device and/or a light illumination heater, and the combinations thereof may be used for required temperature if the temperature is too high or too low.

In an embodiment of the present invention, when the disk 100 is loading on the turn table 113, a unique ID of disk 100 is wirelessly transmitted to the central controller by the RF IC 188, the central controller 101 recognizes that the Nucleic acid amplification disk 100 is loaded.

Nucleic acid amplification chamber 52 of the nucleic acid amplification product readout can be acquired by sending readout information of the fluorescent sensor 152 mounted on the circuit board 140 to the central control processor 101 or the storage unit 112 or the I/O unit 111. Presser 104 is for pressing a disk loaded on the disk air gap 170 by using a magnetic attractive force between the turn table 113 and the disk 100 and configured to move vertically and idle movement. RF power supply device 108 is for supplying a power source to the RF IC 188 with the electromagnetic induction. A LED 150 is a light source for excitation the fluorescent material in the nucleic acid amplification chamber 52.

According to an embodiment of the present invention, the LED 150 may use to excitation the fluorescent material or the temperature sensitive fluorescence dye in the nucleic acid amplification chamber 52.

Laser holes 66 one to one corresponds to the valve and each laser module 103 is embedded in the case 300 310 to independently control the opening and closing of each valve 70, 71, 72, 74, 80 for the laser beam to pass through the case inner wall 310.

Referring to FIGS. 2 and 6, the major process about the nucleic acid amplification disk 100 when the whole blood was used as the sample is as follows.

<Preparation Process>.

According to an embodiment of the present, the chamber where the preparation chamber 24 is for extracting DNA from the whole blood sample, the preparation process is as follows:

1) The blood 10 μl EDTA, ACD Tube or 5 μl Heparin Tube is injected into the centrifugation chamber 20 through the sample inlet port 11 installed at the centrifugation chamber 20.
2) The whole blood is separated into a plasma, a white blood platelet, and the red blood cell while rotating the disk 100 at a high speed. At this time, the most of white blood platelets, and the red blood cell are gathered in the remnant chamber 33. The Sample is detained in the centrifugation chamber 20.
3) If the disk 100 is stopped, the sample in the centrifugation chamber moves into the metering chamber 45 by a hydrophobicity and capillary phenomena. Thus, the metering chamber 45 is filled up and also the part of the sample moving channel 40 is filled up with the sample.
4) The sample in the sample moving channel 40 moves to the trash chamber 23 with the rotation of the disk corresponding to first centrifugal force. Thereafter, the sample in the metering chamber 45 moves to the preparation chamber 24 with the rotation of the disk corresponding to the second centrifugal force.
5) Cell lysis buffer solution for extracting DNA by pulverizing the cell, a Magnetic bead having affinity to the extracted DNA, and the extracting DNA are in the preparation chamber 24. After an incubation for 5 minutes in the preparation chamber 24, DNA is extracted from the cell and deposited to the magnetic bead having affinity to the extracted DNA. The magnetic bead is stationed with a neodymium magnet 60.

6) The valve 71 is opened, if it stops after rotating the disk 100 the wash buffer of the washing chamber 22 fills up the pump channel 7.

7) Thereafter, the wash buffer is flowed into the preparation chamber 24 if the disk 100 is rotated again. When the slider 211 moves near the neodymium magnet 60 while the disk 100 is in rotation, the magnetic bead is cleanse when it meets the permanent magnet 5a on the slider causing it to shake effectively.

8) If the rotation of the disk is stopped the impurity generated in the cell disruption moves to the trash chamber 23 through the check channel 46. At this time, the washing solution in the washing chamber 22 refills the pump channel 7. Thereafter, about 2-3 times 7 and 8 processes are repeated and the washing of the magnetic bead is performed.

9) Thereafter, the valve 70 is opened and the elution buffer or the resuspension buffer in the elution buffer chamber 21 is moved to the preparation chamber 24 with the disk rotation. Through this, DNA bonding to the magnetic bead is separated.

<PCR Process>

According to an embodiment of the present invention, the nucleic acid amplification chamber 52 amplifies DNA is as follows:

1) While the disk 100 is slowly rotated, the valve 80, the valve 74, and valve 72 are opened. DNA deviated from the magnetic bead by the preparation process of in the preparation chamber 24 and the polymerase stored in the polymerase chamber 51 are moved to the nucleic acid amplification chamber 52.

2) The rotation of the disk 100 is stopped after the DNA movement completion to the nucleic acid amplification chamber 52.

3) Thereafter, the nucleic acid amplification disk 100 is heated with the temperature controller 302.

The liquid temperature in the nucleic acid amplification chamber 52 is measured through a change measurement of the cion ink or the temperature sensitive fluorescence dye using the optical sensor 152 or the optical sensor 151 described in the above. In case of the amplification thermo cycle amplification, DNA is repeatedly amplified about 10-30 times and in case of the isothermal amplification, an amplification temperature is preferred to have a constant temperature for about 1-2 hours.

4) Thereafter, the nucleic acid amplification product of the nucleic acid amplification chamber 52 is quantity analyzed by the optical sensor 152 on a real time and the result is stored in the RF IC 188.

All sorts of process for the nucleic acid amplification begin to perform after the auto loading the disk in the turn table 113 if the nucleic acid amplification disk 100 is settled in the tray 333.

The tray 333 is ejected or a warning message is sent to the user when the disk is loading on the turn table 113 without the injection of sample at the sample injection port 11.

The sample injection success or failure can be determined by measuring the transmission rate of centrifugal separation chamber 20 using by the light source 150 or the laser beam and the optical sensor 151. When the sample is injected, success or failure of the injection can be determined because the transmission rate decreases when of failure. If user requests suspension during the nucleic amplification process of nucleic amplification disk, the nucleic amplification device ignores the request and continues its process. It displays a warning message or request password to the user. User's interrupt request is accepted if the password matches.

Moreover, RF IC 188 stores previously used disk recognition information and expiration period information, DNA information to detect or disease information to diagnose. In other words, RC IC 188 records usage history and notifies the user of usage possibility after reloading. Also, it notifies the user of expired nucleic acid amplification disk that cannot be used.

Other aspects, advantages, and salient features of the invention will become apparent to those skilled in the art from the following detailed description, which, taken in conjunction with the annexed drawings, discloses exemplary embodiments of the invention.

It can be also contemplated that various combinations or sub-combinations of the specific features and aspects of the embodiments may be made and still fall within the scope of the appended claims. For example, in some embodiments, the features, configurations, or other details disclosed or incorporated by reference herein with respect to some of the embodiments are combinable with other features, configurations, or details disclosed herein with respect to other embodiments to form new embodiments not explicitly disclosed herein.

All of such embodiments having combinations of features and configurations are contemplated as being part of the present disclosure. Additionally, unless otherwise stated, no features or details of any of the stent or connector embodiments disclosed herein are meant to be required or essential to any of the embodiments disclosed herein, unless explicitly described herein as being required or essential.

Although the present disclosure has been described with an exemplary embodiment, various changes and modifications may be suggested to one skilled in the art. It is intended that the present disclosure encompass such changes and modifications as fall within the scope of the appended claims.

What is claimed:

1. A nucleic acid amplification disk apparatus, comprising:
    a nucleic acid amplification disk, comprising:
        a temperature sensitive synthetic polymer which is a polymer coated with or having absorbed a temperature sensitive fluorescence dye, wherein a fluorescent intensity emitted from the temperature sensitive fluorescence dye is changed according to a temperature,
        a first black film and a second black film both configured to be heated by a laser beam,
        a nucleic acid amplification chamber configured to amplify DNA by isothermal amplification or polymerase chain reaction, in which the temperature sensitive synthetic polymer is coated on one surface of the nucleic acid amplification chamber, and the first black film is coated on another surface of the nucleic acid amplification chamber,
        a preparation chamber configured to get prepare a DNA sample by cell lysis process,
        sub-chambers necessary for nucleic acid amplification,
        a fluid hole and a channel for connecting the sub-chambers,
        a double-sided adhesive tape comprising a first opening of the fluid hole, and
        a substrate comprising a second opening of the fluid hole, which is aligned with the first opening of the fluid hole, wherein the second black film is disposed between the double-sided adhesive tape and the substrate such that the second black film blocks a fluid path between the first opening and the second opening, and wherein the fluid path between the first opening and the second opening is configured to be connected when the second black film is melted by a heat of the laser beam; and a driving controller configured to drive the nucleic acid amplification disk, comprising:
a motor configured to rotate the nucleic acid amplification disk,
a laser beam generator configured to generate the laser beam, and
sensors configured to measure temperature of the nucleic acid amplification chamber by sensing the florescent intensity emitted from the temperature sensitive florescent dye in the nucleic acid amplification chamber.

2. The apparatus of claim 1, the sub-chambers comprise:
a centrifugation chamber for storing the specimen injected through specimen inlet port obtaining sample by removing the remnant with the centrifugation;
a remnant chamber for storing remnant removed from the centrifugation chamber;
a washing chamber for storing washing buffer; and
an elution buffer chamber which stores a re-suspension buffer or an elution buffer for supplying the preparation chamber,
wherein the preparation chamber is further for washing the sample by the washing buffer.

3. The apparatus of claim 2, wherein the preparation chamber further comprising:
a lysis buffer for pulverizing the cell from the sample, and a magnetic bead for linking with an exposed nucleic acid from the pulverized cell by affinity, wherein the washing chamber for washing the magnetic bead and a re-suspension buffer or an elution buffer for eluting a specimen of the DNA are in the preparation chamber.

4. The apparatus of claim 2, wherein the preparation chamber further comprising:
a lysis buffer for pulverizing the cell from the sample and a silica bead for linking with an exposed nucleic acid from the pulverized cell by affinity, wherein the washing chamber for washing the silica bead and are-suspension buffer or an elution buffer for eluting a specimen of the DNA are in the preparation chamber.

5. The apparatus of claim 2, wherein the p nucleic acid amplification disk further comprising:
a sample detainment chamber connected to the centrifugation chamber configured to detain the sample in the centrifugation chamber;
a sample movement channel connected to the sample detainment chamber; and
a metering channel arraigned between the sample movement channel and the preparation chamber to provide a predetermined amount of sample to the preparation chamber.

6. The apparatus of claim 2, wherein the centrifugation chamber is coated with hydrophilicity to help inlet of a hydrophilic sample and the sample movement channel is coated with hydrophilicity to help hydrophilic fluid movement of the detained sample in the detainment channel when the nucleic acid amplification disk is paused.

7. The apparatus of claim 2, the apparatus further comprising:
an isolation channel having a capillary characteristic arranged between the centrifugation channel and the remnant channel, when the nucleic acid amplification disk stops, the separated remnant remains in the remnant chamber due to binding caused by red blood cell viscosity between the remnant chamber and red blood cell and the capillary effect of the isolation chamber.

8. The apparatus of claim 2, wherein the sub-chambers further comprising:
a polymerase chamber connected to the nucleic acid amplification chamber for storing the polymerase; and
the nucleic acid amplification chamber for storing a buffer solution including enzymes, which further including dNTP or primer.

9. The apparatus of claim 8, further comprising:
at least one of valve is arranged between the washing chamber and preparation chamber, the preparation chamber and the elution buffer chamber, the preparation chamber and nucleic acid amplification chamber, and the nucleic acid amplification chamber and the polymerase chamber,
wherein the at least one valve is selectively opened and/or closed with a heat from the laser beam generator.

10. The apparatus of claim 2, further comprising:
a collimator for condensing the fluorescent light emitted from the temperature sensitive fluorescence dye towards the sensors.

11. The apparatus of claim 10, further comprising:
a tape channel is formed of a fluid path shaped double-sided adhesive tape and arranged in between a layer of the substrates.

12. The apparatus of claim 1, wherein the optical sensor is excited by the laser beam generator and measures a temperature of the liquid in the nucleic acid amplification chamber by sensing the fluorescence radiated from the temperature sensitive fluorescence dye within the nucleic acid amplification chamber or quantitatively analyzing the nucleic acid amplification product in the nucleic acid amplification chamber.

13. The apparatus of claim 1, wherein the temperature sensitive fluorescence dye is rhodamine B, perylene, fluorescein, or phosphor.

14. A nucleic acid amplification disk apparatus, comprising: a nucleic acid amplification disk, comprising:
a temperature sensitive synthetic polymer which is a polymer coated with or having absorbed a thermochromic ink made by mixing temperature sensitive pigment, wherein a color of the thermochromic ink is changed according to a temperature,
a first black film and a second black film both configured to be heated by a laser beam, a nucleic acid amplification chamber configured to amplify DNA by isothermal amplification or polymerase chain reaction, in which the temperature sensitive synthetic polymer is coated on one surface of the nucleic acid amplification chamber, and the first black film is coated on another surface of the nucleic acid amplification chamber,
a preparation chamber configured to prepare a DNA sample by cell lysis process,
sub-chambers necessary for nucleic acid amplification,
a fluid hole and a channel for connecting the sub-chambers,
a double-sided adhesive tape comprising a first opening of the fluid hole, and a substrate comprising a second opening of the fluid hole, which is aligned with the first opening of the fluid hole, wherein the second black film is disposed between the double-sided adhesive tape and the substrate such that the second black film blocks a fluid path between the first opening and the second opening, and wherein the fluid path between the first opening and the second opening is configured to be connected when the second black film is melted by a heat of the laser beam; and a driving controller configured to drive the nucleic acid amplification disk, comprising:

a motor configured to rotate the nucleic acid amplification disk, a laser beam generator configured to generate the laser beam, and sensors configured to measure temperature of the nucleic acid amplification chamber by sensing the color of the thermochromic ink.

15. The apparatus of claim 1, the apparatus further comprising:

one or more temperature sensor chamber(s) for measuring a temperature of an ambient air of the nucleic acid amplification disk; and a polymer temperature sensitive polymer synthesis or a thermochromics ink is integrated in the one or more temperature sensor chamber(s).

16. The apparatus of claim 12, wherein the light source or the laser beam generator is used as a heat source apparatus for opening and closing the fluid hole between chambers, the light illuminating heater for heating the nucleic acid amplification chamber, or a light source excites fluorescent labeled DNA of the fluorescent product for quantitative analysis of amplified DNA product in the nucleic acid amplification chamber.

17. The apparatus of claim 1, wherein the optical sensors are any one of an optical sensor for detecting an opening or closing of the fluid hole with the measurement of the transmission light amount through the fluid hole or a fluorescent intensity measurement of the temperature sensitive polymer synthesis and a fluorescence sensor for quantitatively analyzing a fluorescent product for analysis of amplified DNA product in the nucleic acid amplification chamber.

18. The apparatus of claim 1, wherein the nucleic acid amplification disk further comprising:

an wireless radio frequency integrated circuit (IC) for storing and transmitting any one of an individual passwords, information about the usage history of the nucleic acid amplification disk, a validity period information of the nucleic acid amplification disk, DNA type to analyze or a disease information to diagnose, and a read result information about the nucleic acid amplification product, and a disk ID.

19. The apparatus of claim 1, wherein the driving controller further comprising:

a turn table for mounting the nucleic acid amplification disk;

a tray for an input/out of the turn-table; and a case for encapsulating the driving controller.

20. The apparatus of claim 19, wherein the driving controller further includes a temperature controller indirectly controlling a temperature of the nucleic acid amplification chamber by heating or cooling an atmosphere in the nucleic acid amplification chamber or directly controlling a temperature of the nucleic acid amplification chamber by the laser beam generator.

21. The apparatus of claim 1, wherein the first black film or the second black film is an aramid film, a Polyethylene Terephthalate (PET) film, a metallic film having a side coated with black paint, or a polyimide film.

22. The apparatus of claim 20, wherein the temperature controller is any one of a circulation fan for inflowing of an external air, a fan shutter for inflowing of an external air by opening the fan shutter, and a heat emission by a rotation of the nucleic acid amplification disk.

23. The apparatus of claim 19, wherein the nucleic acid amplification disk further comprising: an air temperature sensor provided in the case for measuring temperature of atmosphere, wherein the temperature sensor is any one of a thermocouple, a thermistor, and a laser temperature sensor.

24. The apparatus of claim 1, wherein the sub-chambers comprise:

a DNA sample chambers for temporarily storing a DNA sample injected through a DNA sample inlet;

a phase change material (PCM) chamber is arranged at an entrance and/or an exit of the nucleic acid amplification chamber, a PCM door including a capillary channel;

a trash chamber for storing a redundancy DNA sample after filling up the nucleic acid amplification chamber; and an overflow channel for determining a quantity of the DNA sample requiring for the analysis, and wherein a phase change material (PCM) in the PCM chamber exists in a solid-state, and if the PCM chamber is heated with the laser beam generator, the solid-state PCM turns into a liquid-state PCM and the PCM fills up the capillary channel, and if the PCM chamber heating is paused, the liquid state PCM turns into solid blocking the capillary channel and isolating the nucleic acid amplification chamber from neighboring chambers.

25. The apparatus of claim 19, wherein the case further comprising:

one or more peltier device are arranged between the surface of inside wall and external for heating and cooling the case.

26. The apparatus of claim 1, wherein the driving controller further comprising:

a slider which can move in a radial direction of the nucleic acid amplification disk and mounts the laser beam generator thereon; and a slide motor for controlling the slider.

27. The apparatus of claim 1, the driving controller comprising:

the slider moving in a radial direction of the nucleic acid amplification disk, and permanent magnet on the slider, a thin film cylinder magnet providing the reference space addressing of the fluid hole or the chambers within the nucleic acid amplification disk, wherein the radial direction search of the thin film cylinder magnet is performed by the movement of the slider, wherein the radial direction search of the chambers or the fluid hole can be performed by the magnetic attraction between the permanent magnet and the thin film cylinder magnet.

28. The apparatus of claim 4, the apparatus further comprises a permanent magnet, while washing the silica beads using the washing buffer integrating DNA with the silica bead while removing the remnant from the preparation chamber by stirring the magnetic ball by the magnetic force between the permanent magnetic and the magnetic ball.

29. The apparatus of claim 1, further comprising while the nucleic acid amplification disk is in rotation, azimuth reference hole or reference marker, an azimuth measuring reference for real time measurement, is located on the same radius as the nucleic acid amplification chamber.

30. The apparatus of claim 29, wherein the reference marker is a barcode, which includes a light permeability portion, a light non-permeability portion, and identification (ID) information of the nucleic acid amplification disk.

31. The apparatus of claim 1, the apparatus further comprises,
wherein the nucleic acid amplification disk includes a plurality of fluid holes, and
wherein the driving controller further includes a plurality of laser beam module corresponding to the plurality of fluid holes for independently controlling for opening and closing of the plurality of fluid holes.

32. The apparatus of claim 19, wherein the tray further includes the heating coil for heating the nucleic acid amplification chamber.

33. Analysis method using the apparatus of claim 1, the method comprising:
moving nucleic acid in a preparation chamber and polymerase in a polymerase chamber into a nucleic acid amplification chamber when a nucleic acid amplification disk rotating;
heating the nucleic acid amplification chamber by a temperature controller when the nucleic acid amplification disk stops; and
quantitatively analyzing nucleic acid amplification product by measuring a fluorescence emission intensity of the temperature sensitive fluorescence dye coated on the nucleic acid amplification chamber in a real time.

34. The method of claim 33, the method further comprising:
a) prior to the moving nucleic acid in a preparation chamber and polymerase in a polymerase chamber, inputting sample the centrifugal chamber of the nucleic acid amplification chamber;
b) detaining specimens of the inputted samples within the centrifugal chamber when the nucleic acid amplification disk rotates;
c) moving portion of the specimens to the metering chamber by the hydrophilic and capillary effect and the other portion of the specimen moving to the moving channel when the nucleic acid amplification disk stops,
d) using a first centrifugal moving the other portion of the specimen moved to the moving chamber to the trash chamber when the nucleic acid amplification disk rotates;
e) moving the portion of the specimen in the metering chamber to the preparation chamber when the nucleic acid amplification disk rotates at a greater second centrifugal than the first centrifugal;
f) depositing the nucleic acid of the portion of the specimen on the magnetic bead through lysis process after the nucleic acid amplification disk rotation stops,
g) filling the pump channel with washing buffer of the washing chamber when the nucleic acid amplification disk rotation stops;
h) inputting the washing buffer from the pump channel to the preparation chamber nucleic acid amplification rotates;
i) stir washing each time the magnetic bead meets an external permanent magnet nucleic acid amplification rotates;
j) moving material except the nucleic acid within the preparation channel to the trash chamber when the nucleic acid amplification disk stops;
k) repeating g) to j) by a predetermined times; and
l) moving the elution buffer within the elution chamber or resuspension buffer to the preparation chamber breaking the nucleic acid away.

* * * * *